(12) United States Patent
Tsuyuki

(10) Patent No.: US 11,857,158 B2
(45) Date of Patent: Jan. 2, 2024

(54) OPTICAL SYSTEM, ENDOSCOPE APPARATUS AND ENDOSCOPE

(71) Applicant: OLYMPUS CORPORATION, Hachioji (JP)

(72) Inventor: Hiroshi Tsuyuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 727 days.

(21) Appl. No.: 17/009,840

(22) Filed: Sep. 2, 2020

(65) Prior Publication Data

US 2021/0038060 A1  Feb. 11, 2021

Related U.S. Application Data

(63) Continuation of application No. PCT/JP2018/037261, filed on Oct. 4, 2018.

(30) Foreign Application Priority Data

Mar. 6, 2018 (JP) .................. 2018-039711

(51) Int. Cl.
 *G02B 17/04* (2006.01)
 *A61B 1/00* (2006.01)
 (Continued)

(52) U.S. Cl.
 CPC .... *A61B 1/00096* (2013.01); *A61B 1/000095* (2022.02); *A61B 1/05* (2013.01);
 (Continued)

(58) Field of Classification Search
 CPC . A61B 1/00096; A61B 1/000095; A61B 1/05; A61B 1/0655; A61B 1/00045;
 (Continued)

(56) References Cited

U.S. PATENT DOCUMENTS 8,922,634 B2   12/2014   Namii
10,205,888 B2   2/2019   Tsuyuki et al.
(Continued)

FOREIGN PATENT DOCUMENTS

JP   H1196583 A   4/1999
JP   2000047029 A   2/2000
(Continued)

OTHER PUBLICATIONS

International Search Report (ISR) (and English language translation thereof) dated Jan. 8, 2019 issued in International Application No. PCT/JP2018/037261.

(Continued)

*Primary Examiner* — Euncha P Cherry
(74) *Attorney, Agent, or Firm* — Holtz, Holtz & Volek PC

(57) ABSTRACT

An optical system includes in order from an object side, an objective optical system, a λ/4 wavelength plate including one birefringent material, a polarizing beam splitter which splits light from the objective optical system into two, and an image sensor which picks up two images split. The polarizing beam splitter causes to occur an axial astigmatism of an opposite sign with respect to an axial astigmatism occurred due to the λ/4 wavelength plate, the following conditional expression (1) is satisfied.

$$1.1 \leq Fno/(d/|\Delta n|) \leq 49 \qquad (1)$$

where,
Fno denotes an effective F-number of the objective optical system,
d denotes a thickness of the λ/4 wavelength plate, and
Δn denotes a birefringence of the λ/4 wavelength plate for an e-line, provided that, |0.01|<Δn.

20 Claims, 24 Drawing Sheets

(51) Int. Cl.
*A61B 1/05* (2006.01)
*G02B 27/28* (2006.01)
*G02B 23/24* (2006.01)
*A61B 1/06* (2006.01)
(52) U.S. Cl.
CPC ........ *A61B 1/0655* (2022.02); *G02B 23/2407* (2013.01); *G02B 23/2484* (2013.01); *G02B 27/283* (2013.01)
(58) Field of Classification Search
CPC ... A61B 1/07; A61B 1/00006; A61B 1/00186; A61B 1/00188; A61B 1/051; G02B 23/2407; G02B 23/2484; G02B 27/283; G02B 5/04; G02B 5/30; G02B 13/04; G02B 23/26
See application file for complete search history.

(56) References Cited

U.S. PATENT DOCUMENTS

| | | | | |
|---|---|---|---|---|
| 2007/0211605 | A1* | 9/2007 | Sakamoto | G02B 9/12 369/112.24 |
| 2011/0237999 | A1* | 9/2011 | Muller | A61F 9/00 351/215 |
| 2013/0235174 | A1 | 9/2013 | Namii | |
| 2015/0002646 | A1 | 1/2015 | Namii | |
| 2017/0187943 | A1 | 6/2017 | Tsuyuki et al. | |
| 2020/0018947 | A1* | 1/2020 | Tsuyuki | G02B 27/0075 |

FOREIGN PATENT DOCUMENTS

| | | |
|---|---|---|
| JP | 2005164652 A | 6/2005 |
| JP | 5393926 B2 | 1/2014 |
| JP | 6023919 B2 | 11/2016 |
| WO | 2017073292 A1 | 5/2017 |
| WO | 2018173412 A1 | 9/2018 |

OTHER PUBLICATIONS

Written Opinion dated Jan. 8, 2019 issued in International Application PCT/JP2018/037261.

International Preliminary Report on Patentability (IPRP) (and English language translation thereof) dated Sep. 8, 2020, issued in counterpart International Application No. PCT/JP2018/037261.

* cited by examiner

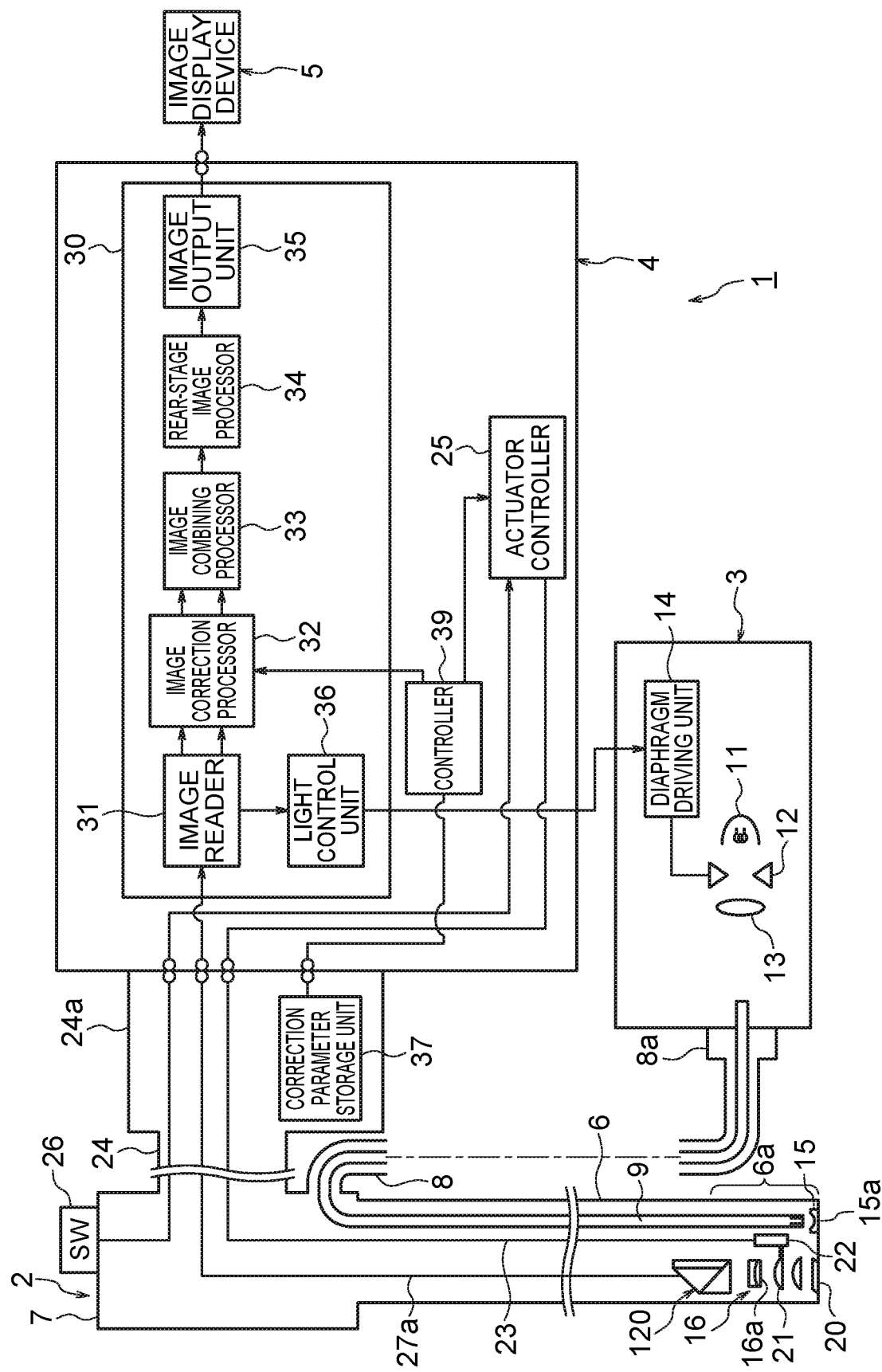

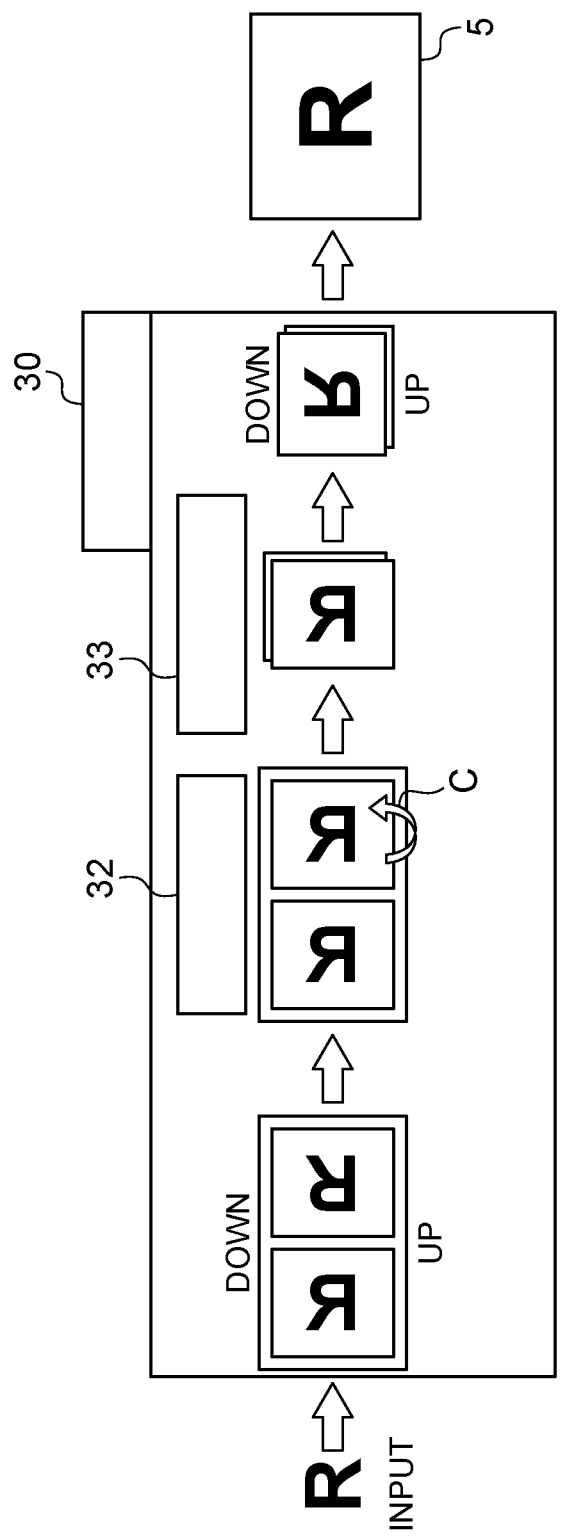

OPTICAL SYSTEM, ENDOSCOPE APPARATUS AND ENDOSCOPE

CROSS-REFERENCE TO RELATED APPLICATION

The present application is a continuation of PCT/JP2018/037261, filed on Oct. 4, 2018 which is based upon and claims the benefit of priority from Japanese Patent Application No. 2018-039711 filed on Mar. 6, 2018; the entire contents of which are incorporated herein by reference.

BACKGROUND

Technical Field

The present disclosure relates to an optical system, an endoscope apparatus and an endoscope.

Description of the Related Art

Generally, in an instrument including an image sensor, such as an endoscope apparatus, it has been known that with an increase in the number of pixels of the image sensor, a depth of field becomes narrow. In other words, in an image sensor, when a pixel pitch (vertical and horizontal dimensions of one pixel) is made small for increasing the number of pixels, as a permissible circle of confusion also becomes small, the depth of field of the image pickup apparatus becomes narrow.

For widening the depth of field, an arrangement in which, for example, a self-image is divided to form images, and images acquired are combined by image processing and the depth is enlarged, has been proposed. Here, at the time of dividing the self-image, using an optical-path splitting unit in which polarization is used is effective. In the optical-path splitting unit in which polarization is used, it is desirable to make light in which the polarization state is depolarized incident on the optical-path splitting unit. An arrangement of such element which depolarizes the polarization state is disclosed in Japanese Patent No. 05393926 Publication and Japanese Patent No. 6023919 Publication.

Japanese Patent No. 05393926 Publication discloses an arrangement in which a λ/4 wavelength plate is disposed between an objective optical system and a polarizing beam splitter. Japanese Patent No. 6023919 discloses a specific arrangement of a depolarization plate.

SUMMARY

An optical system according to the present disclosure includes in order from an object side, an objective optical system, a λ/4 wavelength plate including one birefringent material, a polarizing beam splitter which splits light from the objective optical system into two, and an image sensor which picks up two images split, wherein the polarizing beam splitter causes to occur an axial astigmatism of opposite sign, with respect to an axial astigmatism occurred due to the λ/4 wavelength plate, and the following conditional expression (1) is satisfied, $$1.1 \leq Fno/(d/|\Delta n|) \leq 49 \quad (1)$$

where,

Fno denotes an effective F-number of the objective optical system, d denotes a thickness of the λ/4 wavelength plate, and Δn denotes a birefringence of the λ/4 wavelength plate for an e-line (546.1 nm), provided that, $|0.01| < \Delta n$.

An endoscope apparatus according another aspect of the present disclosure includes the abovementioned optical system, and an image processor having an image combining section which combines images picked up by the image sensor to one image.

Furthermore, an endoscope according to another aspect of the present disclosure includes the abovementioned optical system.

BRIEF DESCRIPTION OF THE DRAWINGS

FIG. 23 is a functional block diagram showing a configuration of the endoscope apparatus according to the embodiment;

FIG. 25 is a diagram showing an imaging state in a case in which an image is formed on an image sensor after reflection for the odd number of times by a beam splitter, in the endoscope apparatus according to the embodiment.

DETAILED DESCRIPTION

An optical system, an endoscope apparatus and an endoscope according to an embodiment will be described below in detail by referring to the accompanying diagram. An objective optical system in an endoscope apparatus is used as an example of the optical system. However, the present invention is not restricted by the embodiment described below.

Figure 1:
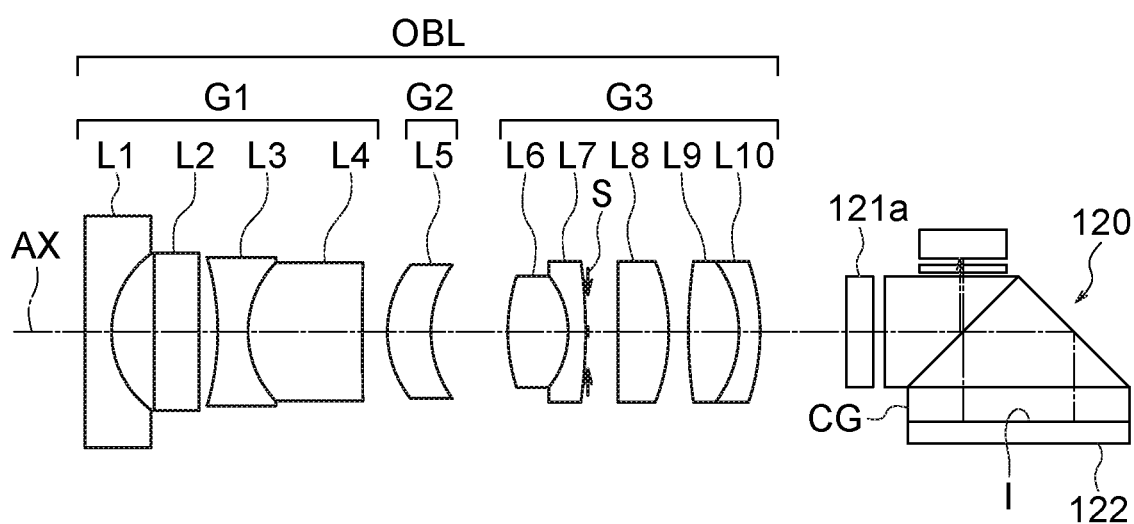
FIG. 1 is a cross-sectional view (normal observation state) of an objective optical system, a λ/4 wavelength plate, an optical-path splitting unit, and an image sensor of an endoscope apparatus according to an embodiment of the present disclosure.

FIG. 1 is a cross-sectional view (normal observation state) of an objective optical system, a λ/4 wavelength plate of higher multi-order, an optical path splitting unit, and an image sensor of the endoscope apparatus according to the present embodiment.

The objective optical system includes in order from an object side, a first lens group G1 having a negative refractive power, a second lens group G2 having a positive refractive power, and a third lens group G3 having a positive refractive power. Moreover, an aperture stop S is disposed in the third lens group G3. The second lens group G2 moves toward an image side on an optical axis AX and corrects a variation in a focal position due to a change from the normal observation state to a close observation state.

The endoscope optical system according to the present embodiment includes in order from the object side, an objective optical system OBL, a λ/4 wavelength plate 121a which includes one birefringent material, polarizing beam splitters 121b and 121e (FIG. 2) which split light from the objective optical system OBL into to two, and an image sensor 122 which picks up two images split, and the endoscope optical system satisfies the following conditional expression (1).

$$1.1 \leq Fno/(d/|\Delta n|) \leq 49 \tag{1}$$

where,

Fno denotes an effective F-number of the objective optical system, d denotes a thickness of the λ/4 wavelength plate, and Δn denotes a birefringence of the λ/4 wavelength plate for an e-line (546.1 nm), provided that, $|0.01|<\Delta n$.

The λ/4 wavelength plate 121a which includes a single birefringent material is a λ/4 wavelength plate of higher multi-order. The λ/4 wavelength plate of higher multi-order has a function of a depolarization plate. By using a material having a large birefringence for the λ/4 wavelength plate of higher multi-order, it is possible to generate a phase difference of even higher order, and to regard a polarized wave for which an intensity of an extraordinary light ray (S-polarized light) and an intensity of an ordinary light ray (P-polarized light) varies at a high frequency in accordance with the wavelength, as equivalent to unpolarized light in a visible range (400 nm-700 nm).

Figure 2:
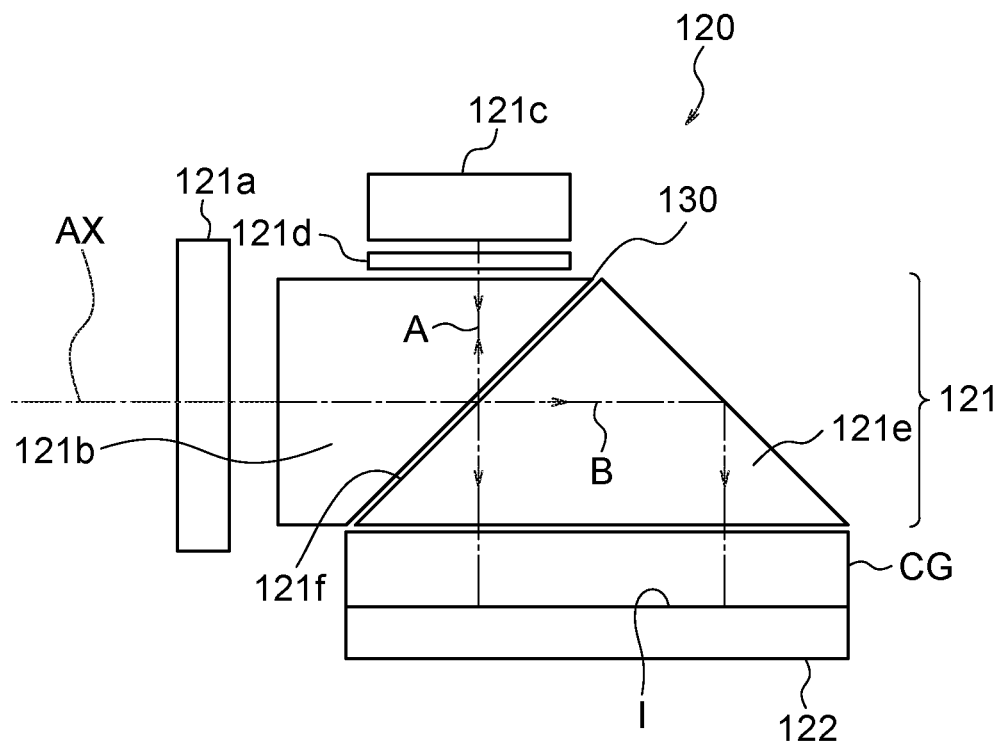
FIG. 2 is a schematic arrangement diagram of a λ/4 wavelength plate of a higher multi-order, the optical-path splitting unit, and the image sensor of the endoscope apparatus according to the embodiment of the present disclosure.

FIG. 2 is a diagram showing a schematic arrangement of the λ/4 wavelength plate 121a of higher multi-order, an optical path splitting unit 120, and an image sensor 122.

Light emerged from the objective optical system OBL passes through the λ/4 wavelength plate 121a of higher multi-order, and is incident on the optical-path splitting unit 120.

The optical-path splitting unit 120 includes a polarizing beam splitter 121 which splits an object image into two optical images of different focus, and the image sensor 122 which acquires two images by picking up the two optical images.

The polarizing beam splitter 121, as shown in FIG. 2, includes an object-side prism 121b, an image-side prism 121e, a mirror 121c, and a λ/4 plate 121d. Both the object-side prism 121b and the image-side prism 121e have a beam splitting surface which is inclined at 45 degrees with respect to the optical axis AX.

Moreover, the object-side prism 121b and the image-side prism 121e are cemented to an adhesive layer 130 by an adhesive.

A polarization splitting film 121f is formed on the beam splitting surface of the object-side prism 121b. Moreover, the object-side prism 121b and the image-side prism 121e form the polarizing beam splitter 121 which brings the beam splitting surfaces in contact via the polarization splitting film 121f.

Furthermore, the mirror 121c is provided near an end surface of the object-side prism 121b via the λ/4 plate 121d. The image sensor 122 is attached to an end surface of the image-side prism 121e via a cover glass CG. Here, I is an image forming surface (image pickup surface).

An object image from the objective optical system OBL is split into a P-polarized component (transmitted light) and an S-polarized component (reflected light) by the polarization splitting film 121f provided on the beam splitting surface of the object-side prism 121b, and are split into two optical images, an optical image of the P-polarized light component and an optical image of the S-polarized light component.

The optical image of the S-polarized light component is reflected at the polarization splitting film 121f toward a surface facing the image sensor 122 and follows an optical path A, and upon being transmitted through the λ/4 plate 121d, is reflected at the mirror 121c, and is returned toward the image sensor 122. The optical image returned, by being retransmitted through the λ/4 plate 121d, has a direction of polarization turned through 90°, and upon being transmitted through the polarization splitting film 121f, is formed as an image on the image sensor 122.

The optical image of the P-polarized light component follows an optical path B upon being transmitted through the polarization splitting film 121, and is reflected by a mirror surface provided on an opposite side of a beam splitting surface of the image-side prism 121e returning perpendicularly toward the image sensor 122, and is formed as an image on the image sensor 122. At this time, an optical path in a glass of the prism is to be set to generate a predetermined optical-path difference of about tens of μm for example in the optical path A and the optical path B, and two optical images of different focus are formed on a light-receiving surface of the image sensor 122.

In other words, the object-side prism 121b and the image-side prism 121e are to be disposed such that an optical-path length on a reflected-light side becomes shorter (smaller) with respect to an optical path length (path length in glass) on a transmitted-light side reaching the image sensor 122 in the object-side prism 121b in order to be able to split the two optical images of different focusing positions of the object image.

Figure 3:
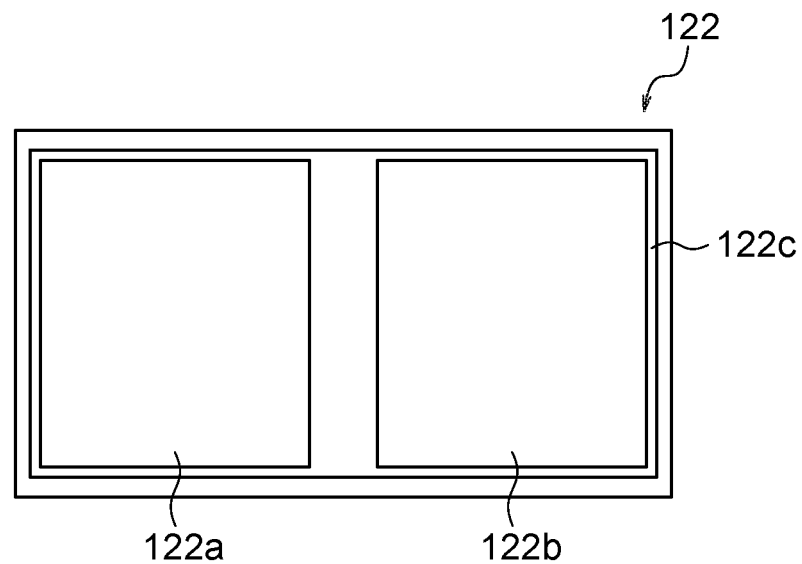
FIG. 3 is a schematic arrangement diagram of the image sensor of the endoscope apparatus according to the embodiment of the present disclosure.

FIG. 3 is a schematic arrangement diagram of the image sensor 122. The image sensor 122, as shown in FIG. 3, is provided with two light receiving areas (effective pixel areas) 122a and 122b in an overall pixel area of the image sensor 122 for capturing an image by receiving separately the two optical images of different focusing positions.

Figure 4A:
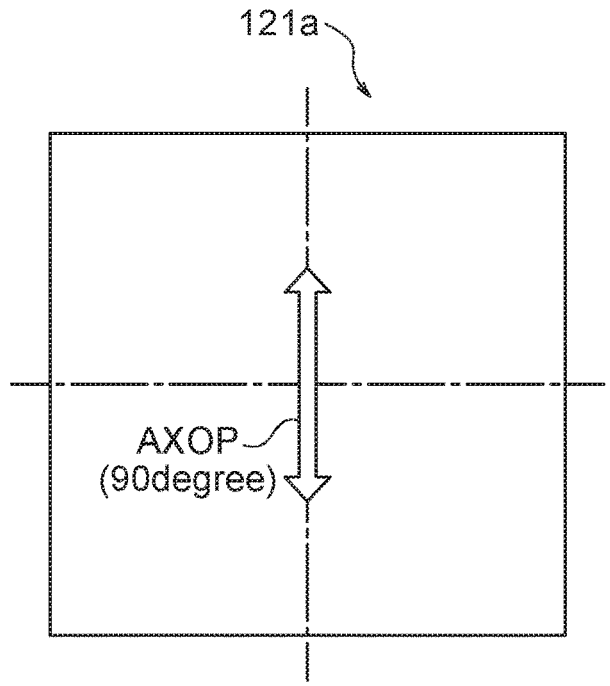
FIG. 4A, FIG. 4B, FIG. 4C, and FIG. 4D are diagrams describing the λ/4 wavelength plate.
Figure 4B:
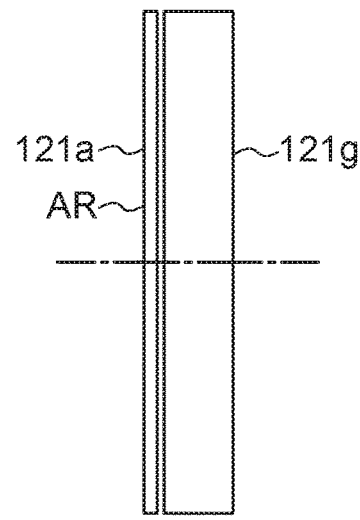
Figure 4C:
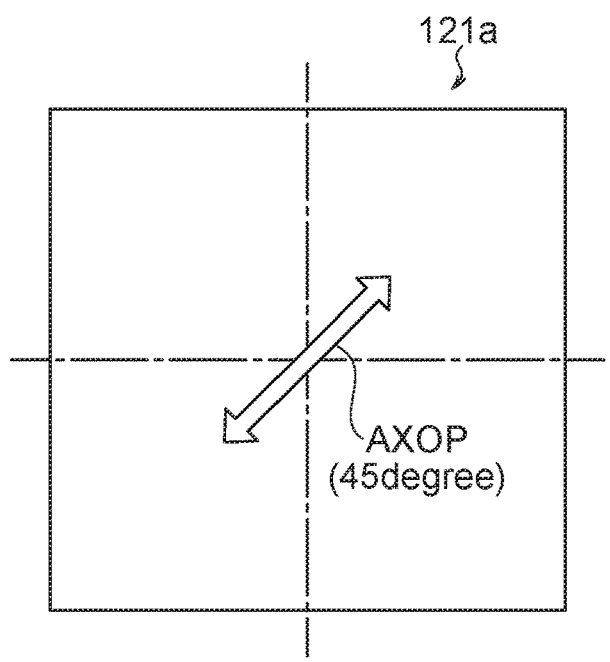
Figure 4D:
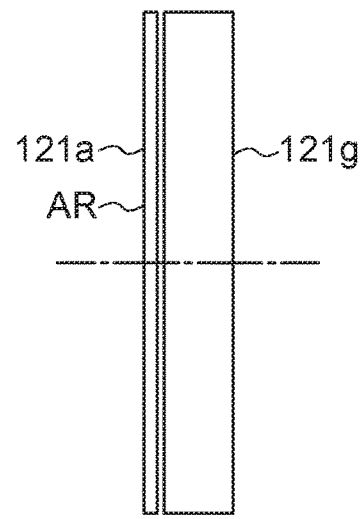

FIG. 4A shows a front view of the λ/4 wavelength plate 121a (optical axis 90 degree) of higher multi-order and FIG. 4B shows a cross-sectional view. FIG. 4C shows a front view of the λ/4 wavelength plate 121a (optical axis 45 degree) of higher multi-order, and FIG. 4D shows a cross-sectional view.

Moreover, an anti-reflection coating AR is applied to an object-side surface of the λ/4 wavelength plate 121a of higher multi-order. Accordingly, it is possible to reduce problems such as a flare, a ghost, and a loss of brightness. Note that, the anti-reflection coating AR may be applied even to a side of a surface of the λ/4 wavelength plate 121a of higher multi-order, cemented to a glass substrate 121g.

Next, a reason as to why it is not possible to achieve a favorable image due an astigmatism which occurs in a depolarization plate in a case of making an attempt to achieve a depolarization effect in an endoscope optical system of a conventional arrangement will be described below.

Figure 5A:
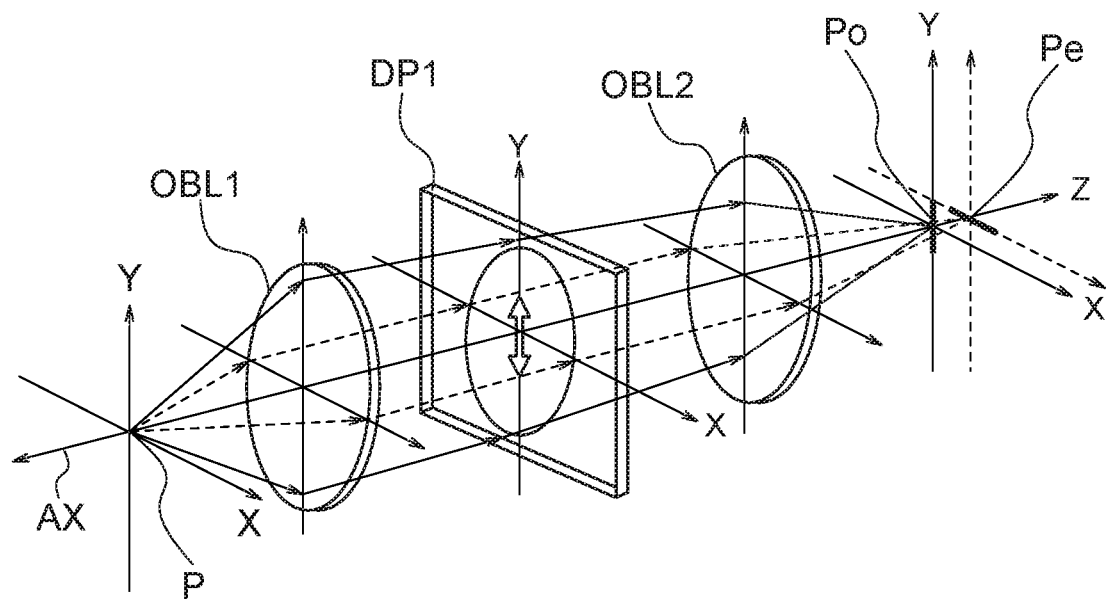
FIG. 5A is a diagram describing an astigmatism which occurs in the λ/4 wavelength plate of higher multi-order.

FIG. 5A shows an astigmatism which occurs in a λ/4 wavelength plate DP1 of higher multi-order. An object point P shows an optical system which forms an image. Light rays from the object point P form an image via objective lenses OBL1 and OBL2. Here, the λ/4 wavelength plate (uniaxial crystal) DP1 of higher multi-order is disposed in an optical path between the objective lens OBL1 and the objective lens OBL2. Accordingly, a position of an image forming point Po of ordinary light and a position of an image forming point Pe of extraordinary light differ.

At this time, when an index ellipsoid having an optical axis in a Y-direction is taken into consideration, a refractive index becomes ne all the time for a light ray in an XZ plane. Whereas, the refractive index for a light ray in an YZ plane becomes no. A refraction effect of a light ray differs for an X-direction and a Y-direction in accordance with an angle of the light ray incident on the λ/4 wavelength plate DP1 of higher multi-order. Consequently, an astigmatism occurs even axially only in a direction of an optical axis. This occurrence of astigmatism can be ignored in a λ/4 wavelength plate of low order or zero order in which a crystal and the like is used, but cannot be ignored in a λ/4 wavelength plate of higher multi-order with large birefringence.

Figure 5B:
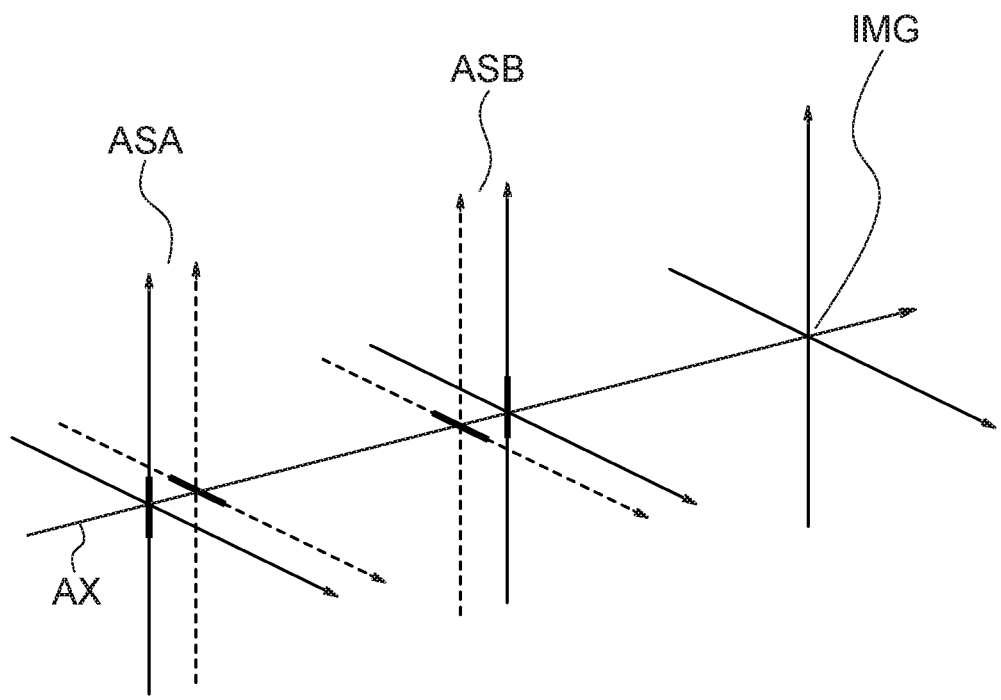
FIG. 5B is a diagram describing the astigmatism which occurs in the λ/4 wavelength plate of higher multi-order and an astigmatism which occurs in a polarizing beam splitter.

FIG. 5B is a diagram describing an astigmatism which occurs in the λ/4 wavelength plate of higher multi-order and an astigmatism which occurs in a polarizing beam splitter. An astigmatism ASA indicated by solid lines and dashed lines occurs in the λ/4 wavelength plate 121a (depolarization plate) (not shown in FIG. 5B). An astigmatism ASB indicated by solid lines and dashed lines occurs in the polarizing beam splitter. An absolute value of aberration amount for the astigmatism ASA and an absolute value of aberration amount for the astigmatism ASB are substantially same, and signs thereof are opposite.

Consequently, the astigmatism ASA+the astigmatism ASB=0, and image forming points in an image sensor IMG coincide.

As mentioned above, by using the λ/4 wavelength plate 121a (depolarization plate) of higher multi-order with a large birefringence, it is possible to achieve a pseudo-depolarization effect. Whereas, by increasing a thickness of the λ/4 wavelength plate 121a of higher multi-order, it is possible to enhance the depolarization effect. However, as a light ray incident on the λ/4 wavelength plate 121a of higher multi-order goes on inclining, the astigmatism occurs even axially only in the direction of the optical axis. In other words, an amount of astigmatism which occurs is determined by a magnitude of the birefringence and a thickness of the λ/4 wavelength plate 121a of higher multi-order, and an angle of incidence on the λ/4 wavelength plate of higher multi-order.

Next, conditional expression (1) of the present embodiment will be explained below. Conditional expression (1) regulates the most appropriate range of $Fno/(d/|\Delta n|)$.

When a value falls below a lower limit value of conditional expression (1), the angle of incidence of a light ray on the λ/4 wavelength plate 121a of higher multi-order becomes excessively large. Or, the λ/4 wavelength plate 121a of higher multi-order being excessively thick, the axial astigmatism becomes excessively large. As a result, an image quality is degraded. Moreover, the birefringence is excessively small, and it is not possible to achieve a favorable depolarization effect.

Whereas, when an upper limit value of conditional expression (1) is exceeded, the objective optical system becomes excessively dark (the F-number becomes large). Or, the λ/4 wavelength plate 121a of higher multi-order is excessively thin, and it is not possible to achieve an adequate depolarization effect. Or, the birefringence is excessively large, and the astigmatism occurs largely. Consequently, since the image quality is deteriorated, it is not favorable. Note that, the relationship is restricted to $|0.01|<\Delta n$. It is desirable that a material to be used for the λ/4 wavelength plate of higher multi-order is a material having a large birefringence to some extent. For a material having a small birefringence such as a crystal and the like, an amount of phase difference that occurs is excessively small, and when the material is made thick in order to achieve depolarization effect, it cannot be accommodated in a front-end portion of an endoscope, and therefore it is not favorable.

Moreover, according to a preferable aspect of the present embodiment, it is desirable that the λ/4 wavelength plate is disposed between an aperture stop of the objective optical system and an optical-path splitting surface of the polarizing beam splitter.

The closer the angle of incidence of a light ray incident on the λ/4 wavelength plate of higher multi-order to parallel to the optical axis, the more suppressible is the occurrence of astigmatism. In a wide angle retro focus optical system such as an endoscope, an angle of oblique incidence of an off-axis ray becomes excessively large on a front-group side of the aperture stop. Therefore, when the λ/4 wavelength plate of higher multi-order is disposed on the front-group side, since a large astigmatism occurs even for the off-axis, it is not preferable. Consequently, it is desirable to dispose the λ/4 wavelength plate of higher multi-order on an image plane side on a rear side of the aperture stop, and between the front side (object side) of the polarizing beam splitter.

Moreover, according to a preferable aspect of the present embodiment, it is desirable to cause an axial astigmatism of an opposite sign to occur in the polarizing beam splitter, with respect to an axial astigmatism occurred in the λ/4 wavelength plate.

When an oblique incidence light is incident on a crystal material of a large birefringence, an astigmatism AS occurs in a direction of an optical axis. In the λ/4 wavelength plate of higher multi-order, light incident on the polarizing beam splitter becomes an unpolarized astigmatism because of having the depolarization effect. For light split into two by the polarizing beam splitter, the astigmatism AS is included evenly in a P-polarized light optical path and an S-polarized light optical path.

Whereas, the adhesive layer 130 which joins the polarizing beam splitters 121b and 121e is disposed to be inclined (wedge shape) with respect to an incident light ray. Consequently, another astigmatism B (ASB in FIG. 5B) occurs due to a difference in a refractive index of the polarizing beam splitter and a refractive index of the adhesive of the adhesive layer. At this time, when a magnitude of an absolute value of the astigmatism A (ASA in FIG. 5B) and a magnitude of an absolute value of the astigmatism B are substantially same, and the astigmatism is of opposite signs (opposite directions), they cancel each other. As a result, it is possible to reduce the astigmatism to an amount that can be made almost zero at the image forming surface (light receiving surface of the image sensor).

Moreover, according to a preferable aspect of the present embodiment, it is desirable that the λ/4 wavelength plate is a uniaxial crystal material having a negative birefringence.

In the uniaxial crystal material having a negative birefringence, the relationship between the refractive index no of the ordinary light and the refractive index ne of the extraordinary light becomes no>ne. When the a λ/4 wavelength plate of higher multi-order having a negative birefringence which is a uniaxial crystal material, is used, an astigmatism of a sign opposite to that of the astigmatism which occurs in the adhesive layer which is inclined with respect to an incident light ray at the polarizing beam splitter occurs. Consequently, it is possible to cancel the astigmatism.

Moreover, according to a preferable aspect of the present embodiment, it is desirable that the optical system satisfies the following conditional expression (2).

$$0.8 \leq (np/\Delta n)/(d/lpc) \leq 4.4 \quad (2)$$

where, np denotes a refractive index for an e-line (546.1 nm) of a glass material used for the polarizing beam splitter, Δn denotes a birefringence of the λ/4 wavelength plate for the e-line (546.1 mm), provided that, $|0.01|<\Delta n$, d denotes a thickness of the λ/4 wavelength plate, and lpc denotes a thickness of an adhesive layer of an adhesive used on a surface of the polarizing beam splitter.

It is possible to control the amount of astigmatism which occurs, by the refractive index of the glass material used for the polarizing beam splitter, the thickness of the adhesive layer, the birefringence of the crystal material used for the wavelength plate, and the thickness of the crystal material used for the wavelength plate.

When a value falls below a lower limit value of conditional expression (2), the thickness of the λ/4 wavelength plate becomes excessively thick. Or, by the birefringence becoming excessively large, it is not possible to cancel the astigmatism. Consequently, an image is deteriorated.

When an upper limit value of conditional expression (2) is exceeded, the thickness of the λ/4 wavelength plate becomes excessively thin, and the most appropriate aberration correction becomes difficult. Moreover, a problem related to processing of the λ/4 wavelength plate arises. Or, the refractive index of the glass material used for the polarizing beam splitter becomes excessively high and the astigmatism which occurs in the polarizing beam splitter becomes excessively large, and it is not possible to cancel the astigmatism. Consequently, an image is deteriorated.

An endoscope optical system in an endoscope apparatus according to an example 1 will be described below.

Figure 6:
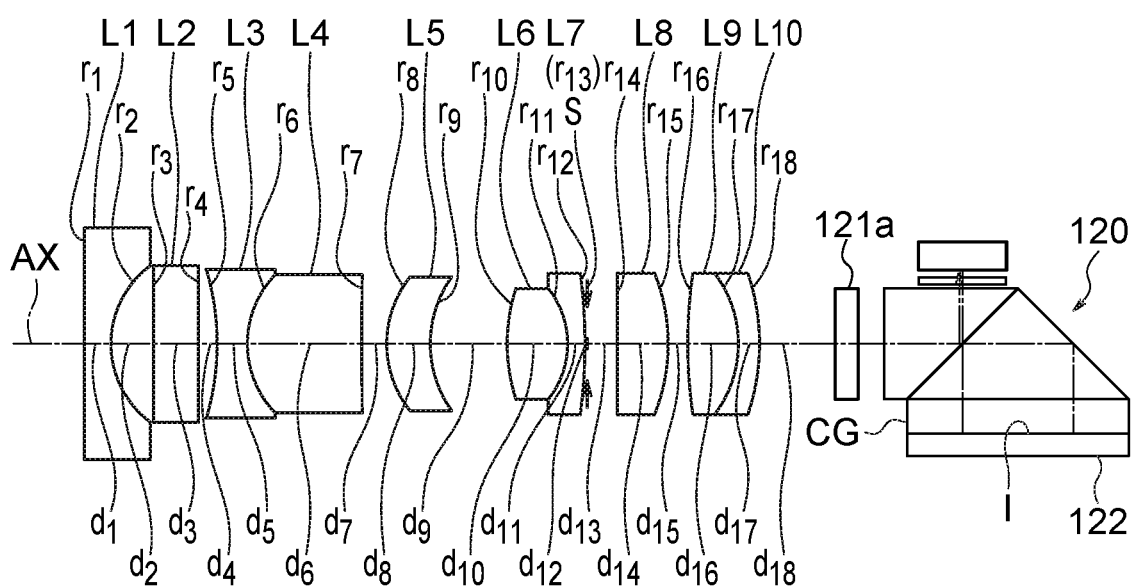
FIG. 6 is a cross-sectional view of a lens arrangement of an endoscope optical system according to an example 1.

FIG. 6 is a cross-sectional view of an objective optical system, a λ/4 wavelength plate of higher multi-order, an optical-path splitting unit, and an image sensor. Here, FIG. 6 is a cross-sectional view showing an arrangement of the objective optical system in a normal observation state (an object point at a far distance). It is possible to switch the objective optical system to a close observation state (an object point at a close distance) by driving a lens L5.

The objective optical system includes in order from an object side, a planoconcave negative lens L1 having a flat surface directed toward the object side, a plane parallel plate L2, a biconcave negative lens L3, a positive meniscus lens L4 having a convex surface directed toward the object side, a positive meniscus lens L5 having a convex surface directed toward the object side, a biconvex positive lens L6, a negative meniscus lens L7 having a convex surface directed toward an image side, an aperture stop S, a biconvex positive lens L8, a biconvex positive lens L9, and a negative meniscus lens L10 having a convex surface directed toward the image side. Here, the biconcave negative lens L3 and the positive meniscus lens L4 are cemented. The biconvex positive lens L6 and the negative meniscus lens L7 are cemented. The biconvex positive lens L9 and the negative meniscus lens L10 are cemented.

The abovementioned optical-path splitting unit 120 is disposed on the image side of the objective optical system. In a prism in the optical system, an optical path is bent. Note that, the plane parallel plate L2 is a filter having a coating for cutting specific wavelengths such as, 1060 nm of YAG (yttrium aluminum garnet) laser, 810 nm of semiconductor laser, or an infrared region applied thereto. I is an image forming surface (image pickup surface).

Moreover, the λ/4 wavelength plate 121a of higher multi-order is disposed on the image side of the objective optical system, between the objective optical system and the optical-path splitting unit 120.

Numerical data for each example is shown below. Regarding symbols, r denotes a radius of curvature of each lens surface, d denotes a distance between two lens surfaces, ne denotes a refractive index for an e-line of each lens, ve denote Abbe's number of each lens, FNO denotes an F-number, and ω denotes a half angle of view. Moreover, a back focus fb is expressed by a distance from an optical surface nearest to image up to a paraxial image plane being subjected to air conversion. An overall length is a length obtained by adding the back focus to a distance (not subjected to air conversion) from a lens surface nearest to object up to an optical surface nearest to image. A stop is an aperture stop.

Numerical data for the example is shown below.

Example 1

Unit mm

Surface data

| Surface no. | r | d | ne | ve |
|---|---|---|---|---|
| 1 | ∞ | 0.49 | 1.88815 | 40.52 |
| 2 | 1.812 | 0.79 | | |
| 3 | ∞ | 0.84 | 1.52300 | 66.3 |
| 4 | ∞ | 0.34 | | |
| 5 | −4.881 | 0.56 | 1.88815 | 40.52 |
| 6 | 1.866 | 2.13 | 1.85504 | 23.59 |
| 7 | 77.332 | Variable | | |
| 8 | 2.010 | 0.81 | 1.48915 | 70.04 |
| 9 | 2.149 | Variable | | |
| 10 | 3.354 | 1.13 | 1.65222 | 33.53 |
| 11 | −1.665 | 0.32 | 2.01169 | 28.07 |
| 12 | −9.987 | 0.04 | | |
| 13(Stop) | ∞ | 0.56 | | |
| 14 | 512.363 | 0.95 | 1.70442 | 29.89 |
| 15 | −3.552 | 0.36 | | |
| 16 | 9.128 | 0.94 | 1.48915 | 70.04 |
| 17 | −2.180 | 0.39 | 1.93429 | 18.74 |
| 18 | −4.093 | 4.59 | | |
| 19(Image pickup surface) | ∞ | | | |

Various data
Normal observation state

| focal length | 1.00 |
|---|---|
| FNO. | 3.58 |
| 2ω | 144.9 |
| fb (in air) | 4.59 |
| LTL (in air) | 17.15 |
| d7 | 0.47 |
| d9 | 1.43 |

Example 1

Figure 7:
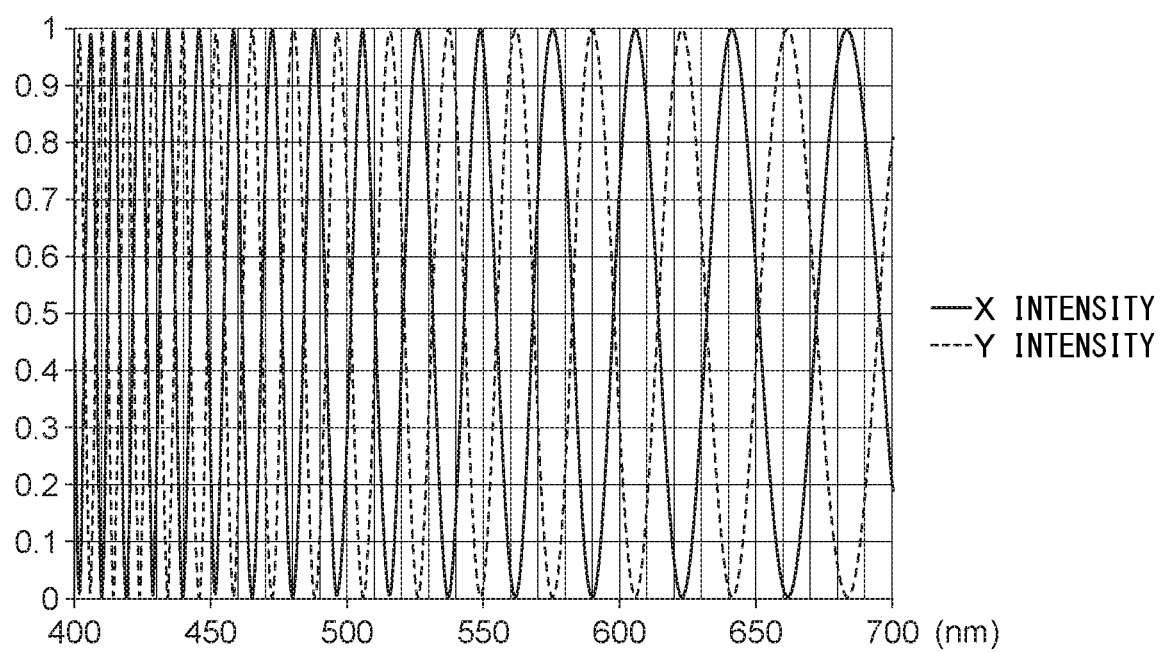
FIG. 7 is a diagram showing an optical characteristic of a λ/4 wavelength plate of higher multi-order of 16 wavelengths in the example 1.

FIG. 7 shows an optical characteristic of a λ/4 wavelength plate 121a of higher multi-order in the endoscope apparatus according to the example 1. The optical characteristic is a wavelength scramble characteristic (depolarization characteristic) in a case in which linearly polarized light is incident on the λ/4 wavelength plate 121a. It is an example of generating a phase difference of 16 wavelengths. Solid lines (intensity X) and dashed lines (intensity Y) indicate respective orthogonal polarization components. A horizontal axis indicates a wavelength (nm) and a vertical axis indicates an intensity of P-polarized light (intensity X for example) and S-polarized light (intensity Y for example) after being transmitted through the λ/4 wavelength plate of higher multi-order. The λ/4 wavelength plate 121a of higher multi-order with a large birefringence is to be disposed between the polarizing beam splitter 121 and an objective optical system OBL of an endoscope, and to be used as a depolarization plate. Light passed through the λ/4 wavelength plate 121a of higher multi-order can be deemed as equivalent to unpolarized light in a visible range (400 nm~700 nm) in a visible region because a polarized wave varies at a high frequency in accordance with the wavelength.

In a zero order λ/4 wavelength plate or a multi-order λ/4 wavelength plate of several wavelengths, although it is possible to convert linearly polarized light of specific wavelength to circularly polarized light, a wavelength and polarization dependency in the entire visible range being high, it is not possible to maintain a split intensity in the polarizing beam splitter, and it is not possible to achieve an image of uniform intensity. By making an arrangement shown in the present example, an adequate depolarization effect is achieved and there is no need to use a depolarization plate having a complex arrangement. Consequently, an advantageous effect that it is possible to realize small-sizing of a distal end of endoscope of an endoscope apparatus is shown.

Figure 8A:
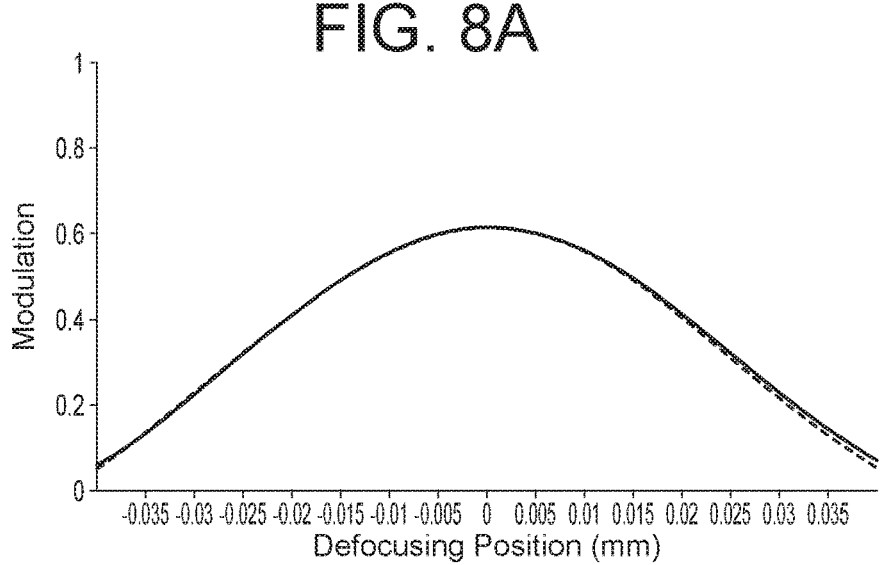
FIG. 8A is a diagram showing an astigmatism achieved finally.
Figure 8B:
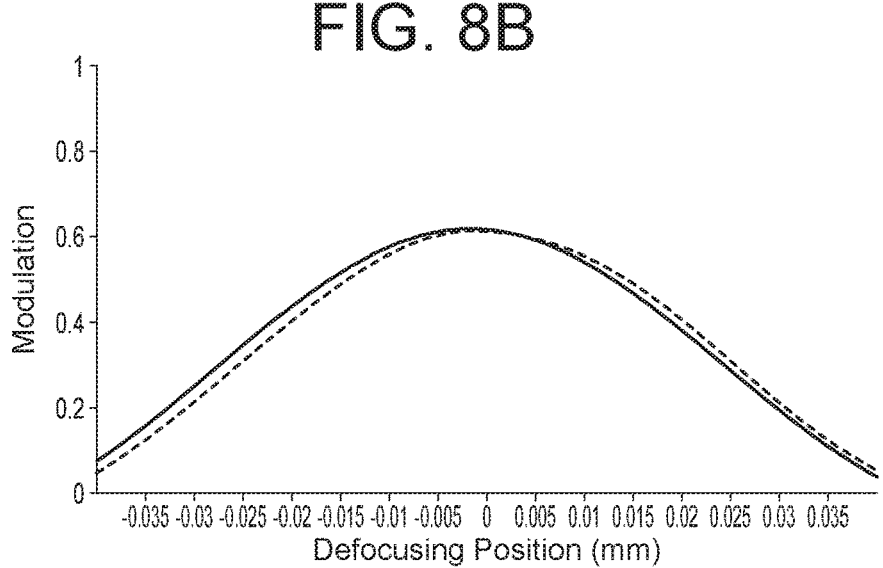
FIG. 8B is a diagram showing an astigmatism in an adhesive layer (wedge portion) of a polarizing beam splitter.
Figure 8C:
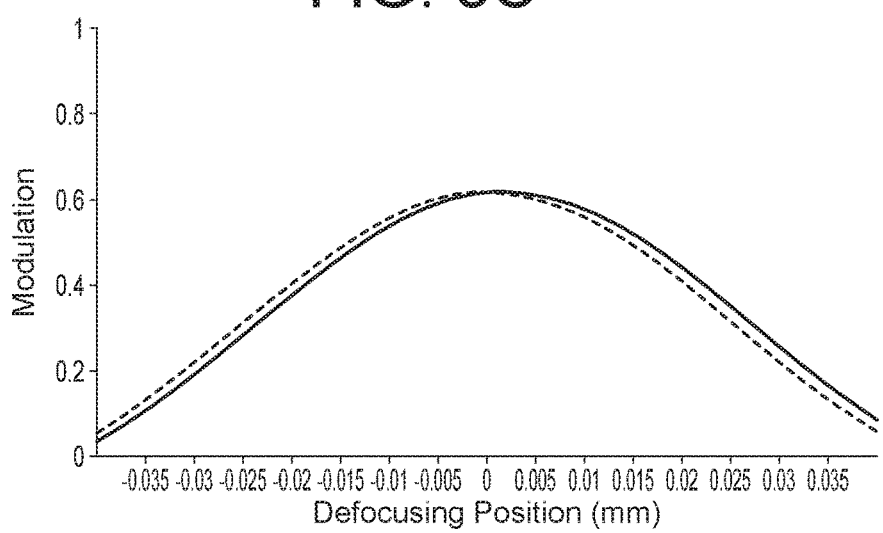
FIG. 8C is a diagram showing an astigmatism in the λ/4 wavelength plate of the higher multi-order, in the example 1.

FIG. 8A, FIG. 8B, and FIG. 8C are diagrams showing an axial MFT (Modulation Transfer Function) in the present embodiment. A horizontal axis indicates a defocusing amount and a vertical axis indicates the MTF. The axial MTF is proportional to the astigmatism. In the diagrams, solid lines indicate the axial MFT in a sagittal direction and dashed lines indicate the MTF in a meridional direction. The diagrams showing the axial MTF in all examples below will indicate in the same manner as in the present example.

FIG. 8A shows an astigmatism at a final image plane. FIG. 8B shows an astigmatism in the adhesive layer 130 of the polarizing beam splitters 121b and 121e. FIG. 8C shows an astigmatism after being transmitted through the λ/4 wavelength plate 121a of higher multi-order.

The astigmatism at the image plane shown in FIG. 8A is obtained by adding a characteristic curve shown in FIG. 8B and a characteristic curve shown in FIG. 8C. As it is evident from FIG. 8A, a difference between an astigmatism in the meridional direction and an astigmatism in the sagittal direction is reduced.

Accordingly, in the present example, it is possible to achieve an adequate depolarization and to reduce the astigmatism which occurs in the λ/4 wavelength plate of higher multi-order, thereby enabling to achieve a favorable image.

Example 2

An endoscope optical system in an endoscope apparatus according to an example 2 will be described below.

Figure 9:
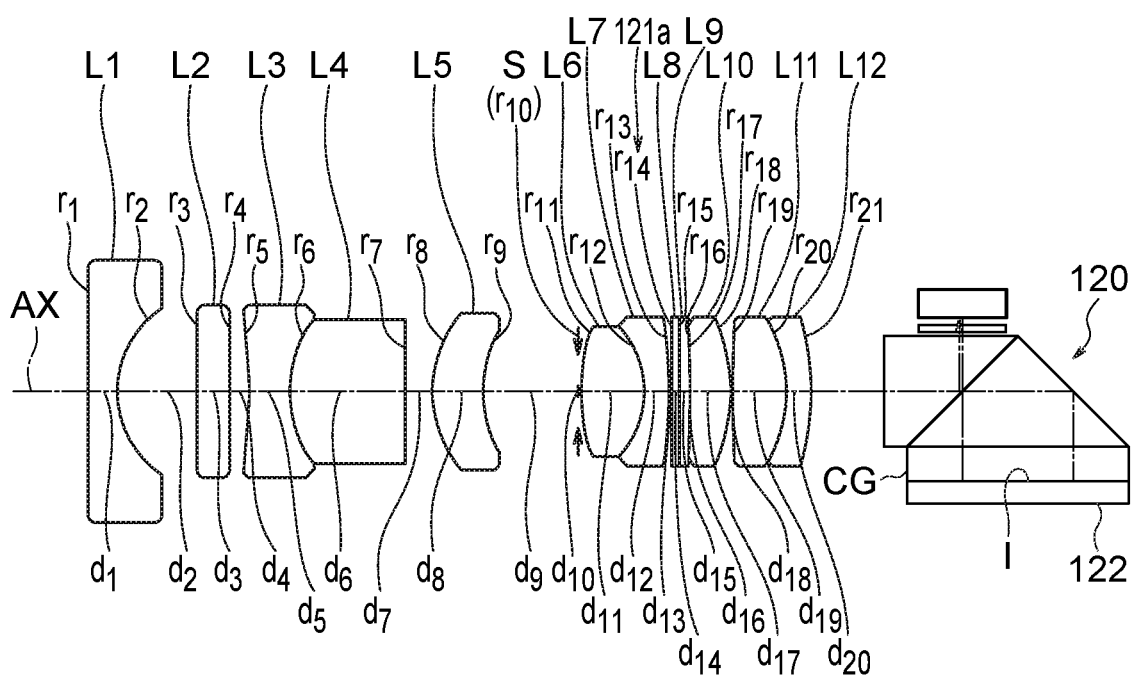
FIG. 9 is a cross-sectional view of a lens arrangement of an endoscope optical system according to an example 2.

FIG. 9 is a cross-sectional view of an objective optical system, a λ/4 wavelength plate of higher multi-order, an optical-path splitting unit, and an image sensor. The λ/4 wavelength plate is disposed in the objective optical system. Here, FIG. 9 is a cross-sectional view showing an arrangement of the objective optical system in a normal observation state (an object point at a far distance). It is possible to switch the objective optical system to a close observation state (an object point at a near distance) by driving a lens L5.

The objective optical system includes in order from an object side, a planoconcave negative lens L1 having a flat surface directed toward the object side, a plane parallel plate L2, a biconcave negative lens L3, a planoconvex positive lens L4 having a convex surface directed toward the object side, a positive meniscus lens L5 having a convex surface directed toward the object side, an aperture stop S, a biconvex positive lens L6, a negative meniscus lens L7 having a convex surface directed toward an image side, a plane parallel plate L8, a plane parallel plate L9, a planoconvex positive lens L10 having a convex surface directed toward the image side, a biconvex positive lens L11, and a negative meniscus lens L12 having a convex surface directed toward the image side. Here, the biconcave negative lens L3 and the planoconvex positive lens L4 are cemented. The biconvex positive lens L6 and the negative meniscus lens L7 are cemented. The plane parallel plate L8 and the plane parallel plate L9 are cemented. The biconvex positive lens L11 and the negative meniscus lens L12 are cemented.

The reason as to why the two plates, the plane parallel plate L8 and the plane parallel plate L9, are cemented is, for improving a handleability of the λ/4 wavelength plate of higher multi-order. For instance, a thickness of $LiNbO_3$ in Example 2 is 0.15 mm, and in an example to be described later, the thickness of $LiNbO_3$ is 0.12 mm which is thin. Therefore, while handling the λ/4 wavelength plate of higher multi-order, a precaution about breakage etc. is necessary. Therefore, by sticking glass plates which are plane parallel plates as in the present example, the handleability of the λ/4 wavelength plate of higher multi-order is improved. A material to be cemented may be a glass substrate, but it is preferable that it is a material such as quartz glass, having a coefficient of linear expansion closer to a coefficient of linear expansion of a material of the λ/4 wavelength plate of higher multi-order.

The abovementioned optical-path splitting unit 120 is disposed on the image side of the objective optical system. In a prism in an objective optical system, an optical path is bent. Note that, the plane parallel plate L2 is a filter having a coating for cutting specific wavelengths such as, 1060 nm of YAG laser, 810 nm of semiconductor laser, or an infrared region, applied thereto. I is an image forming surface (image pickup surface). The λ/4 wavelength plate 121a of higher multi-order is disposed on a $14^{th}$ surface which is a surface of the plane parallel plate L8.

Numerical data for the example is shown below.

Example 2

| | | Unit mm | | |
|---|---|---|---|---|
| | | Surface data | | |
| Surface no. | r | d | ne | ve |
| 1 | ∞ | 0.49 | 1.88815 | 40.52 |
| 2 | 1.6876 | 1.42 | | |
| 3 | ∞ | 0.56 | 1.523 | 66.3 |
| 4 | ∞ | 0.34 | | |
| 5 | −8.2416 | 0.70 | 1.88815 | 40.52 |
| 6 | 1.999 | 2.02 | 1.85504 | 23.59 |
| 7 | ∞ | 0.46 | | |
| 8 | 1.999 | 0.88 | 1.48915 | 70.04 |
| 9 | 2.107 | 1.63 | | |
| 10(Stop) | ∞ | 0.07 | | |
| 11 | 3.9026 | 1.09 | 1.65222 | 33.79 |
| 12 | −1.588 | 0.42 | 2.01169 | 28.27 |
| 13 | −7.6482 | 0.04 | | |
| 14(λ/4 Wavelength plate) | ∞ | 0.15 | 2.31649 | 18.72 |
| 15 | ∞ | 0.15 | 1.51825 | 63.93 |
| 16 | ∞ | 0.03 | | |
| 17 | ∞ | 0.70 | 1.70442 | 29.89 |
| 18 | −2.9908 | 0.03 | | |
| 19 | 17.82 | 0.94 | 1.48915 | 70.04 |
| 20 | −2.3806 | 0.42 | 1.93429 | 18.74 |
| 21 | −5.0866 | 4.56 | | |
| 22(Image pickup surface) | ∞ | | | |

| Various data | |
|---|---|
| focal length | 1 |
| Fno. | 3.6 |
| 2ω | 152.6 |
| fb | 4.56 |
| 14th surface(λ/4 Wavelength plate) $LiNbO_3$ | |

Figure 10:
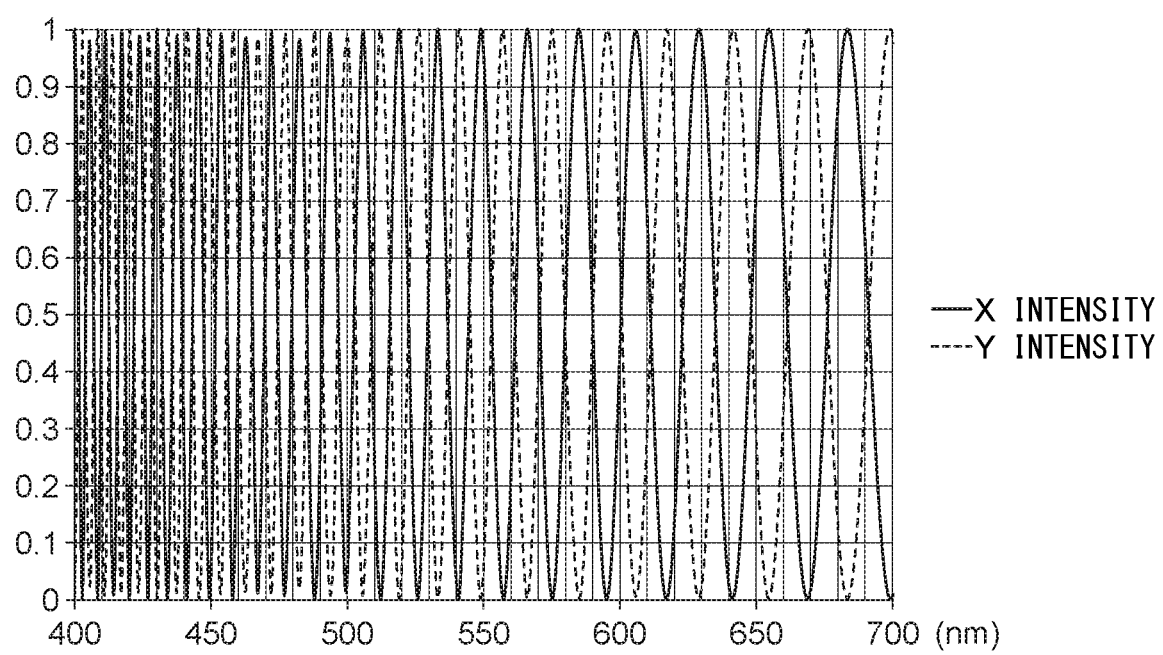
FIG. 10 is a diagram showing an optical characteristic of a λ/4 wavelength plate of higher multi-order of 24 wavelengths in the example 2.

FIG. 10 shows an optical characteristic of the λ/4 wavelength plate of higher multi-order in the endoscope apparatus according to the example 2. It is an example of generating a phase difference of 24 wavelengths. The λ/4 wavelength plate 121a of higher multi-order having a large birefringence is disposed on the $14^{th}$ surface of the objective optical system, and is used as a depolarization plate. For the λ/4 wavelength plate 121a, since a polarized wave varies at a high frequency in accordance with the wavelength, light passed through the λ/4 wavelength plate 121a can be deemed as equivalent to unpolarized light in a visible range (400 nm 700 nm).

Figure 11A:
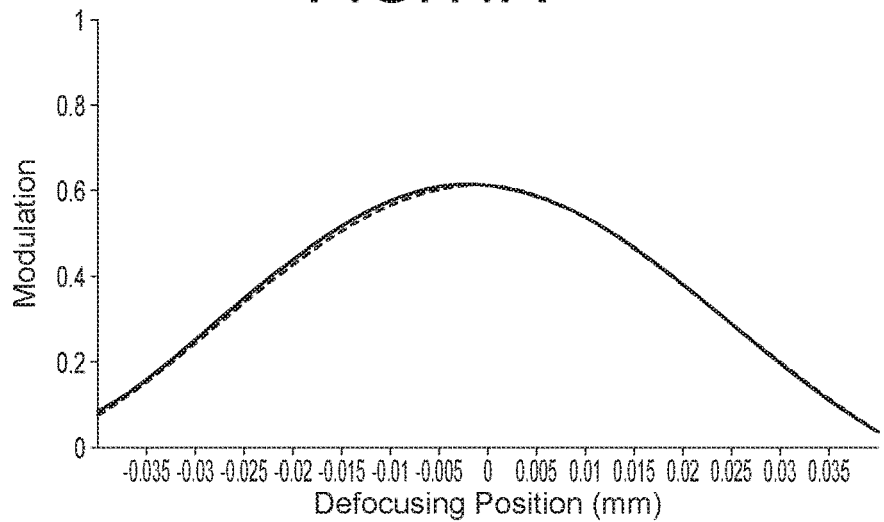
FIG. 11A is a diagram showing an astigmatism achieved finally.
Figure 11B:
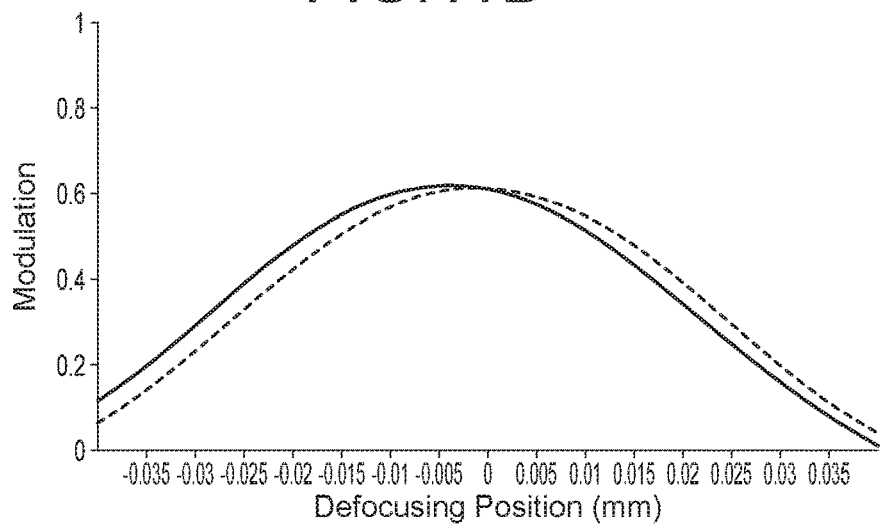
FIG. 11B is a diagram showing an astigmatism in an adhesive layer (wedge portion) of a polarizing beam splitter.
Figure 11C:
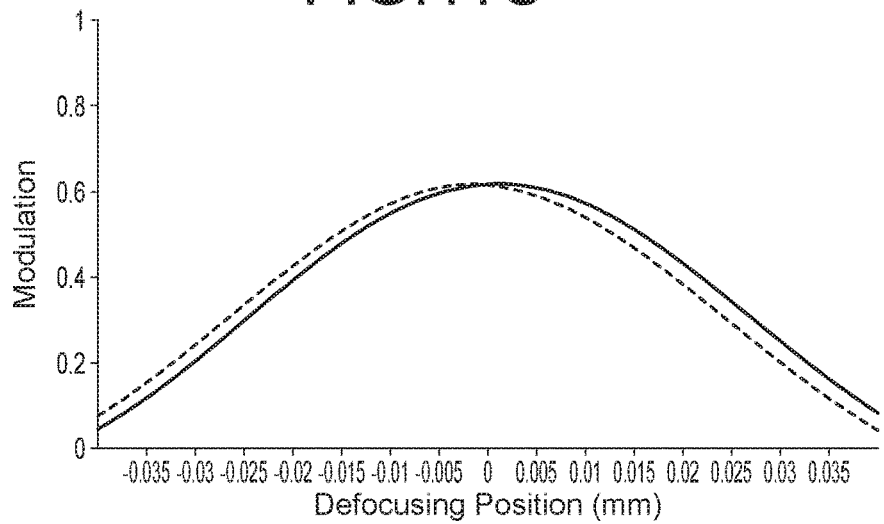
FIG. 11C is a diagram showing an astigmatism in a λ/4 wavelength plate of higher multi-order, in the example 2.

FIG. 11A shows an astigmatism at a final image plane. FIG. 11B shows an astigmatism in an adhesive layer 130 of polarizing beam splitters 121b and 121e. FIG. 11C shows an astigmatism after being transmitted through the λ/4 wavelength plate 121a of higher multi-order.

The astigmatism at the image plane shown in FIG. 11A is obtained by adding a characteristic curve shown in FIG. 11B and a characteristic curve shown in FIG. 11C. As it is evident from FIG. 11A, a difference between an astigmatism in a meridional direction and an astigmatism in a sagittal direction is reduced.

Accordingly, in the present example, it is possible to achieve an adequate depolarization and to reduce the astigmatism which occurs in the λ/4 wavelength plate of higher multi-order, thereby enabling to achieve a favorable image.

Example 3

An endoscope optical system according to an example 3 will be described below. An optical characteristic of a λ/4 wavelength plate 121a of higher multi-order in an endoscope apparatus according to the example 3 is same as that in the example 1 (refer to FIG. 7). Therefore, the description of optical characteristic is omitted.

Figure 12A:
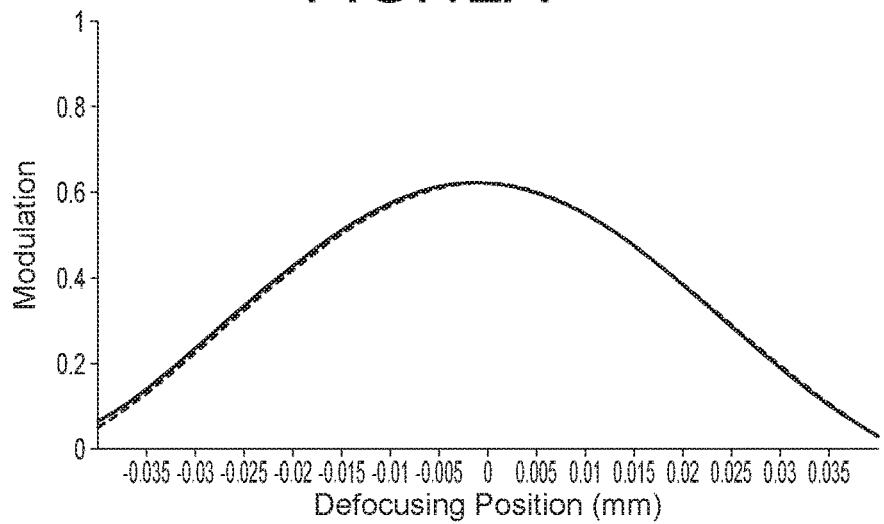
FIG. 12A is a diagram showing an astigmatism achieved finally.
Figure 12B:
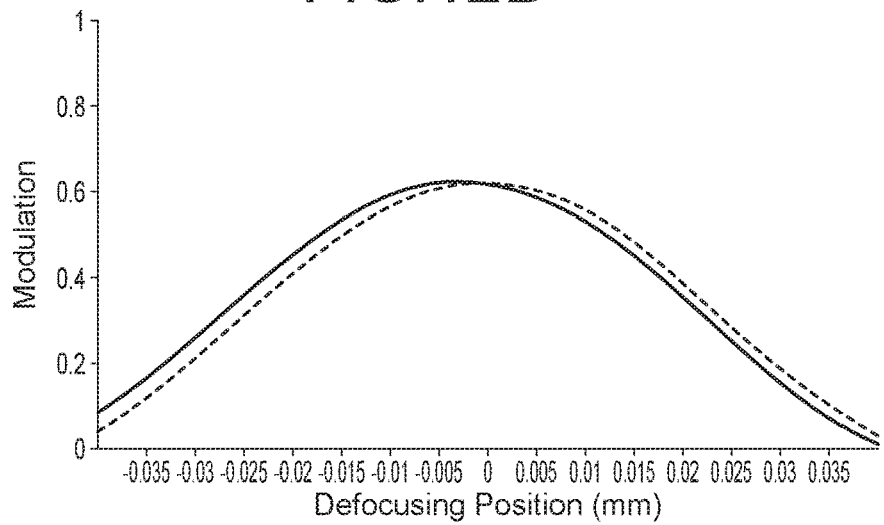
FIG. 12B is a diagram showing an astigmatism in an adhesive layer (wedge portion) of a polarizing beam splitter, and 12C is a diagram showing an astigmatism in a λ/4 wavelength plate of the higher multi-order, in an example 3.
Figure 12C:
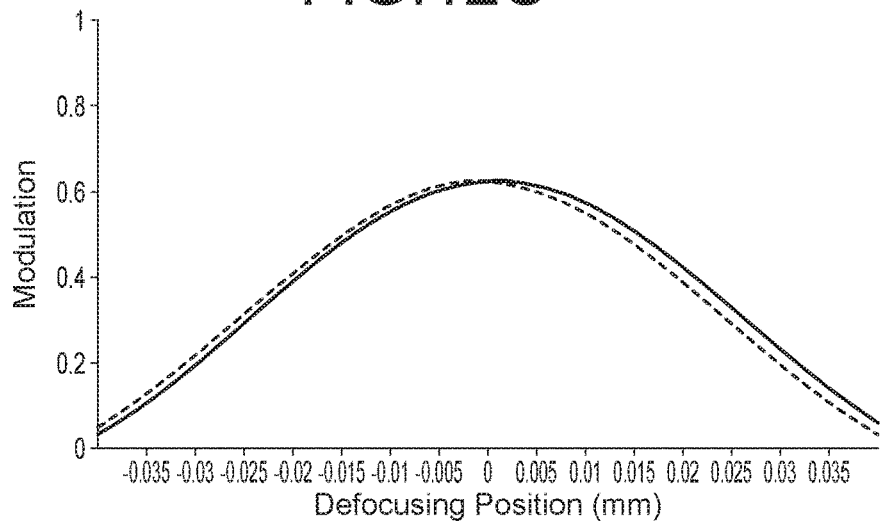

FIG. 12A shows an astigmatism at a final image plane. FIG. 12B shows an astigmatism in an adhesive layer 130 of polarizing beam splitters 121b and 121e. FIG. 12C shows an astigmatism after being transmitted through the λ/4 wavelength plate 121a of higher multi-order.

The astigmatism at the image plane shown in FIG. 12A is obtained by adding a characteristic curve shown in FIG. 12B and a characteristic curve shown in FIG. 12C. As it is evident from FIG. 12A, a difference between an astigmatism in a meridional direction and an astigmatism in a sagittal direction is reduced.

Accordingly, in the present example, it is possible to achieve an adequate depolarization and to reduce the astigmatism which occurs in the λ/4 wavelength plate of higher multi-order, thereby enabling to achieve a favorable image.

Example 4

Figure 13:
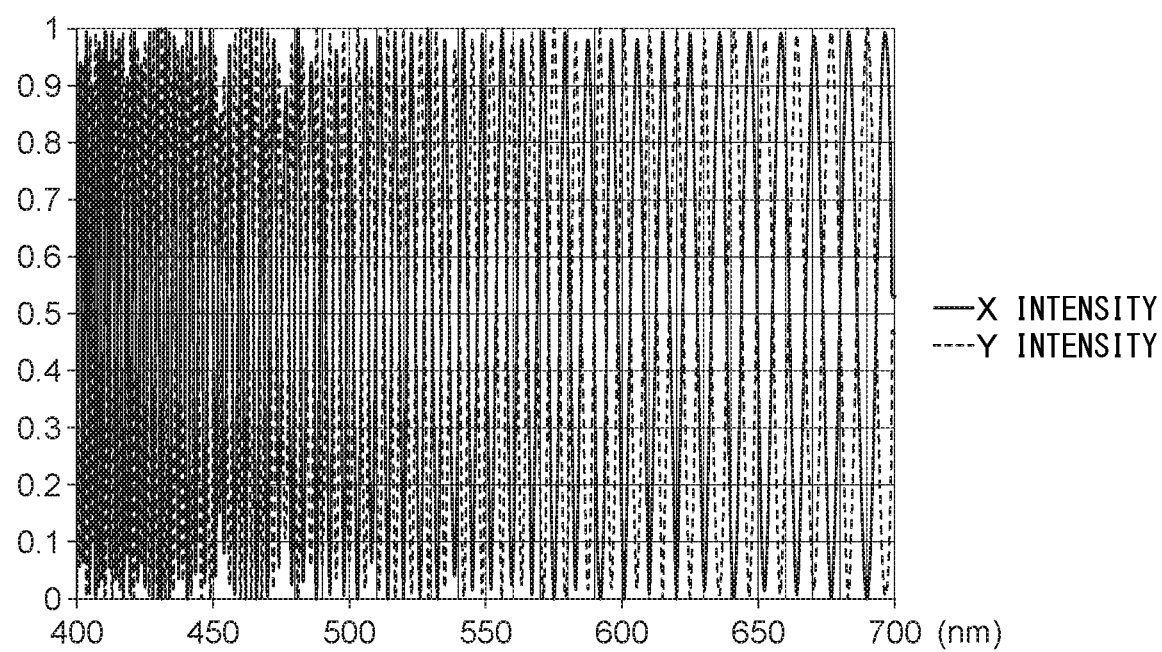
FIG. 13 is a diagram showing an optical characteristic of a λ/4 wavelength plate of higher multi-order of 56 wavelengths in an example 4.

An endoscope optical system according to an example 4 will be described below. FIG. 13 shows an optical characteristic of a λ/4 wavelength plate 121a of higher multi-order in an endoscope apparatus according to the example 4. It is an example of generating a phase difference of 56 wavelengths. The λ/4 wavelength plate 121a of multi-order having a large birefringence is disposed and used as a depolarization plate. For the λ/4 wavelength plate 121a of higher multi-order, since a polarized wave varies at a high frequency in accordance with the wavelength, light passed through the λ/4 wavelength plate of higher multi-order can be deemed as equivalent to unpolarized light in a visible range (400 nm~700 nm).

Figure 14A:
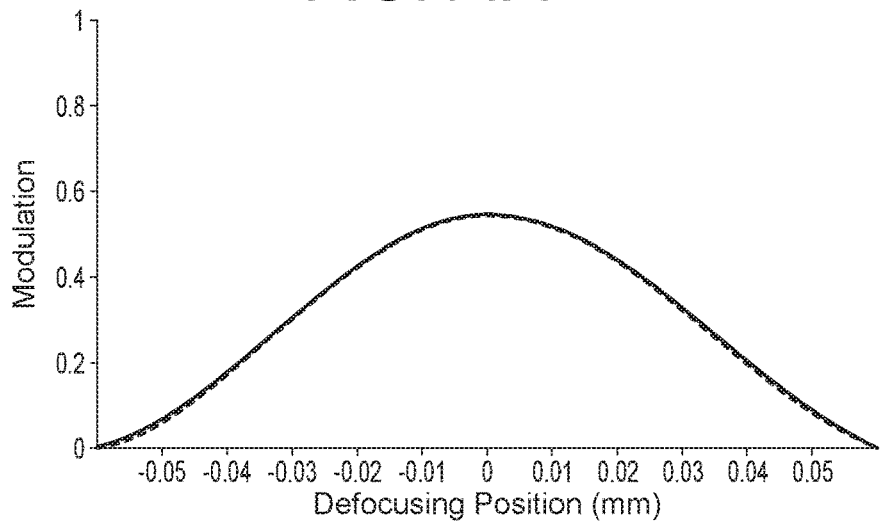
FIG. 14A is a diagram showing an astigmatism achieved finally.
Figure 14B:
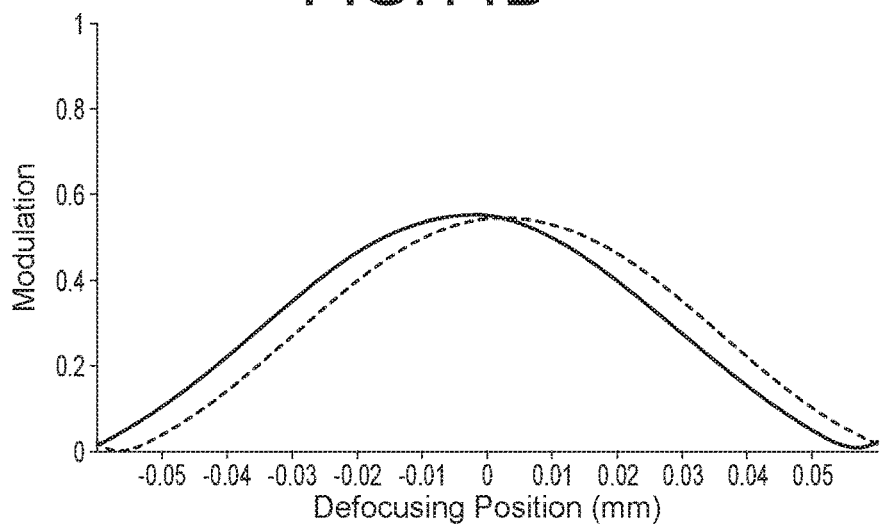
FIG. 14B is a diagram showing an astigmatism in an adhesive layer (wedge portion) of a polarizing beam splitter.
Figure 14C:
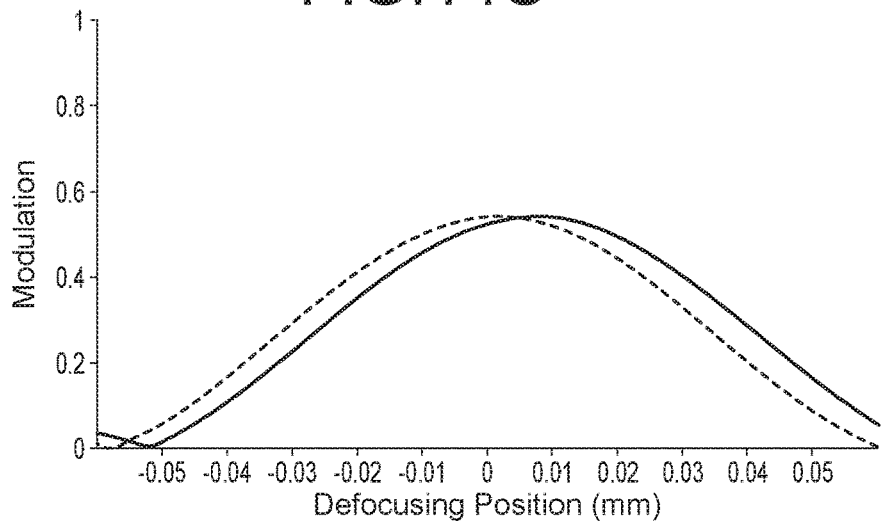
FIG. 14C is a diagram showing an astigmatism in a λ/4 wavelength plate of higher multi-order, in the example 4.

FIG. 14A shows an astigmatism at a final image plane. FIG. 14B shows an astigmatism in an adhesive layer 130 of polarizing beam splitters 121b and 121e. FIG. 14C shows an astigmatism after being transmitted through the λ/4 wavelength plate of higher multi-order.

The astigmatism at the image plane shown in FIG. 14A is obtained by adding a characteristic curve shown in FIG. 14B and a characteristic curve shown in FIG. 14C. As it is evident from FIG. 14A, a difference between an astigmatism in a meridional direction and an astigmatism in a sagittal direction is reduced.

Accordingly, in the present embodiment, it is possible to achieve an adequate depolarization and to reduce the astigmatism which occurs in the λ/4 wavelength plate of higher multi-order, thereby enabling to achieve a favorable image.

Example 5

An endoscope optical system in an endoscope apparatus according to an example 5 will be described below.

Figure 15:
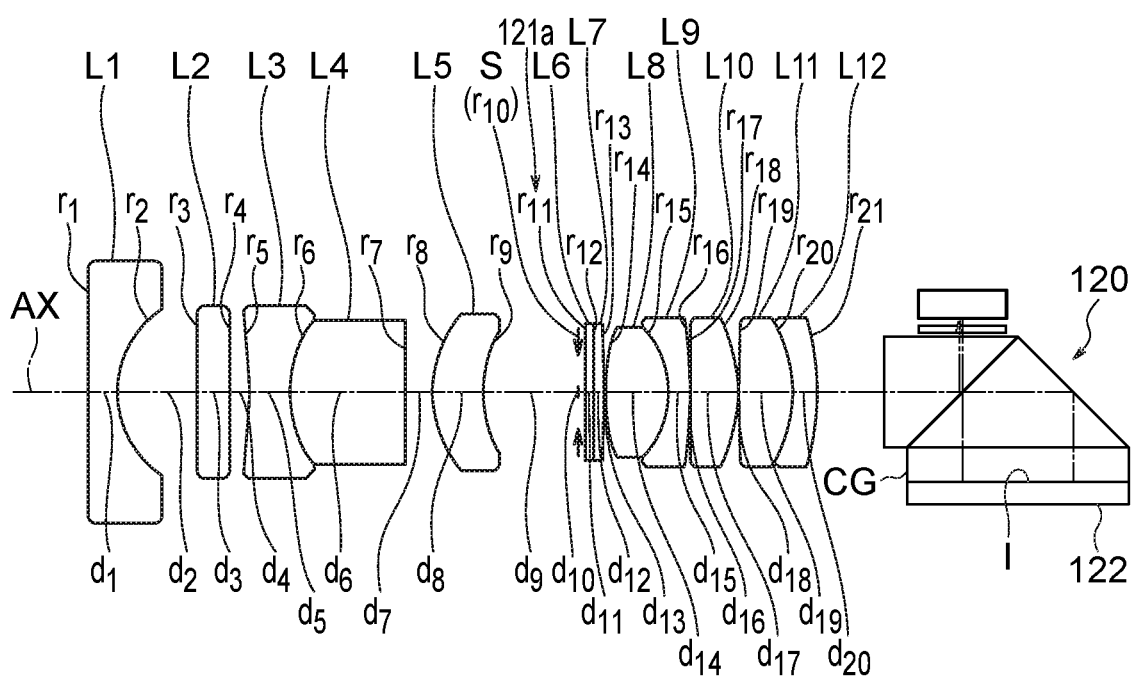
FIG. 15 is a cross-sectional view of a lens arrangement of an endoscope optical system according to an example 5.

FIG. 15 is a cross-sectional view of an objective optical system, a λ/4 wavelength plate of higher multi-order, an optical-path splitting unit, and an image sensor. Here, FIG. 15 is a cross-sectional view showing an arrangement of the objective optical system in a normal observation state (an object point at a far distance). It is possible to switch the objective optical system to a close observation state (an object point at a near distance) by driving a lens L5. A λ/4 wavelength plate 121a of higher multi-order is disposed in the objective optical system.

The objective optical system includes in order from an object side, a planoconcave negative lens L1 having a flat surface directed toward the object side, a plane parallel plate L2, a biconcave negative lens L3, a planoconvex positive lens L4 having a convex surface directed toward the object side, a positive meniscus lens L5 having a convex surface directed toward the object side, an aperture stop S, a plane parallel plate L6, a plane parallel plate L7, a biconvex positive lens L8, a negative meniscus lens L9 having a convex surface directed toward an image side, a planoconvex positive lens L10 having a flat surface directed toward the object side, a biconvex positive lens L11, and a negative meniscus lens L12 having a convex surface directed toward the image side. Here, the biconcave negative lens L3 and the planoconvex positive lens L4 are cemented. The plane parallel plate L6 and the plane parallel plate L7 are cemented. The biconvex positive lens L11 and the negative meniscus lens L12 are cemented.

The abovementioned optical-path splitting unit 120 is disposed on the image side of the objective optical system. In a prism in an optical system, an optical path is bent. Note that, the plane parallel plate L2 is a filter having a coating for cutting specific wavelengths such as, 1060 nm of YAG laser, 810 nm of semiconductor laser, or an infrared region, applied thereto. I is an image forming surface (image pickup surface). The reason as to why the plane parallel plate L6 and the plane parallel plate L7 are cemented is as mentioned above. The λ/4 wavelength plate 121a of higher multi-order is disposed on an 11$^{th}$ surface which is a surface of the plane parallel plate L6. Numerical data for the example is shown below.

Example 5

Unit mm

Surface data

| Surface no. | r | d | ne | ve |
|---|---|---|---|---|
| 1 | ∞ | 0.50 | 1.88815 | 40.52 |
| 2 | 1.7216 | 1.46 | | |
| 3 | ∞ | 0.57 | 1.523 | 66.3 |
| 4 | ∞ | 0.35 | | |
| 5 | −8.5506 | 0.72 | 1.88815 | 40.52 |
| 6 | 2.0726 | 2.01 | 1.85504 | 23.59 |
| 7 | ∞ | 0.47 | | |
| 8 | 2.0507 | 0.92 | 1.48915 | 70.04 |
| 9 | 2.1645 | 1.67 | | |
| 10(Stop) | ∞ | 0.07 | | |
| 11(λ/4 Wavelength plate) | ∞ | 0.12 | 2.31649 | 18.72 |
| 12 | ∞ | 0.18 | 1.51825 | 63.93 |
| 13 | ∞ | 0.03 | | |
| 14 | 3.8932 | 1.15 | 1.65222 | 33.79 |
| 15 | −1.6009 | 0.33 | 2.01169 | 28.27 |
| 16 | −8.7901 | 0.03 | | |
| 17 | ∞ | 0.82 | 1.70442 | 29.89 |
| 18 | −2.9852 | 0.03 | | |
| 19 | 14.9972 | 0.96 | 1.48915 | 70.04 |
| 20 | −2.4888 | 0.36 | 1.93429 | 18.74 |
| 21 | −5.2167 | 4.58 | | |
| 22(Image pickup surface) | ∞ | | | |

Various data

| | |
|---|---|
| focal length | 1 |
| Fno. | 3.6 |
| 2ω | 160.5 |
| fb | 4.53 |
| 11th surface(λ/4 wavelength plate) LiNbO$_3$ | |

Figure 16:
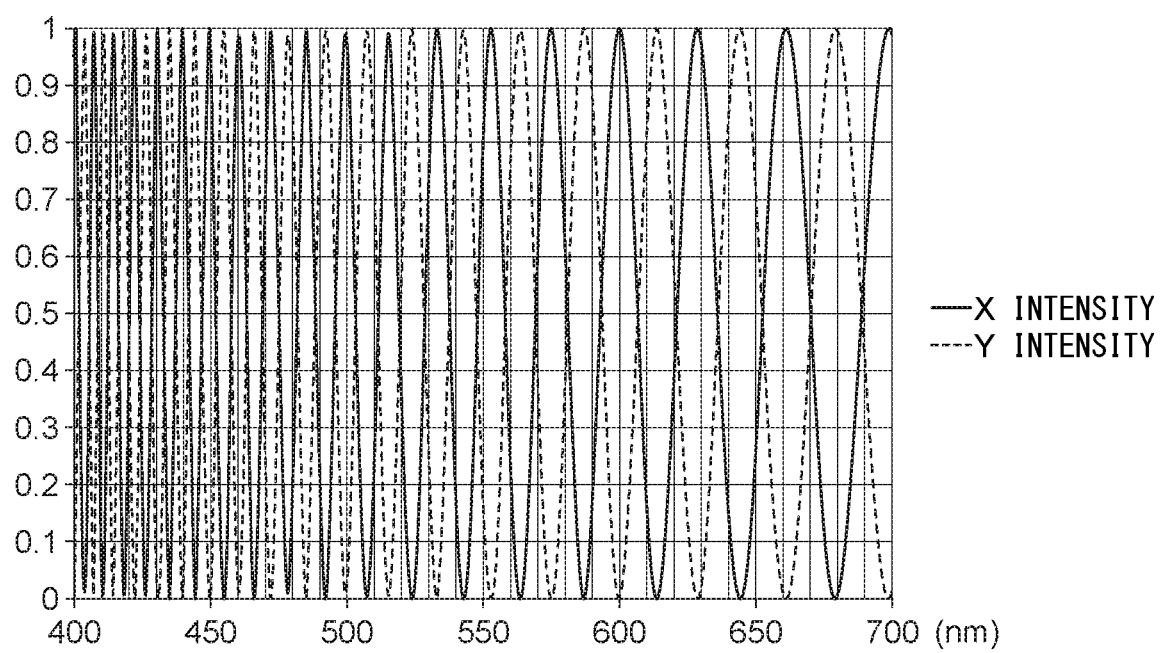
FIG. 16 is a diagram showing an optical characteristic of a λ/4 wavelength plate of higher multi-order of 19 wavelengths in the example 5.

The endoscope optical system according to the example 5 will be described below. FIG. 16 shows an optical characteristic of the λ/4 wavelength plate 121a of higher multi-order in the endoscope apparatus according to the example 5. It is an example of generating a phase difference of 19 wavelengths. The λ/4 wavelength plate 121a of higher multi-order having a large birefringence is disposed and is used as a depolarization plate. For the λ/4 wavelength plate 121a of higher multi-order, since a polarized wave varies at a high frequency in accordance with the wavelength, light passed through the λ/4 wavelength plate 121a can be deemed as equivalent to unpolarized light in a visible range (400 nm 700 nm).

Figure 17A:
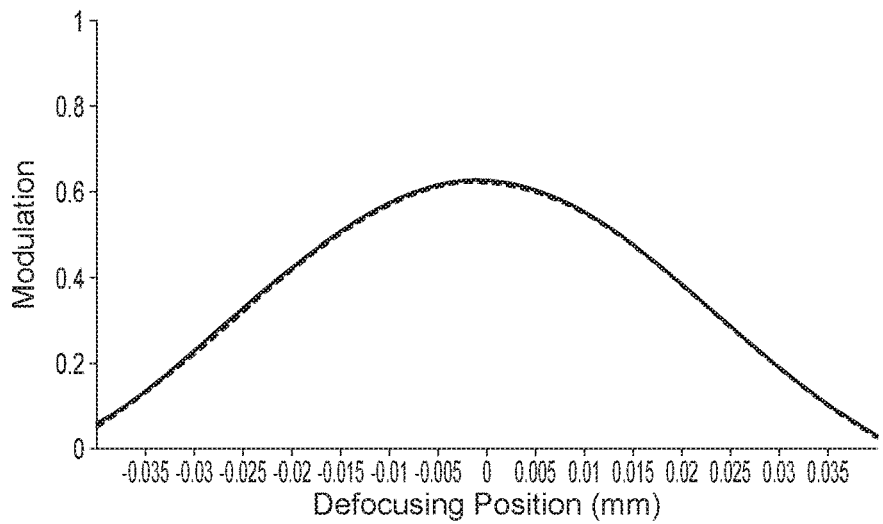
FIG. 17A is a diagram showing an astigmatism achieved finally.
Figure 17B:
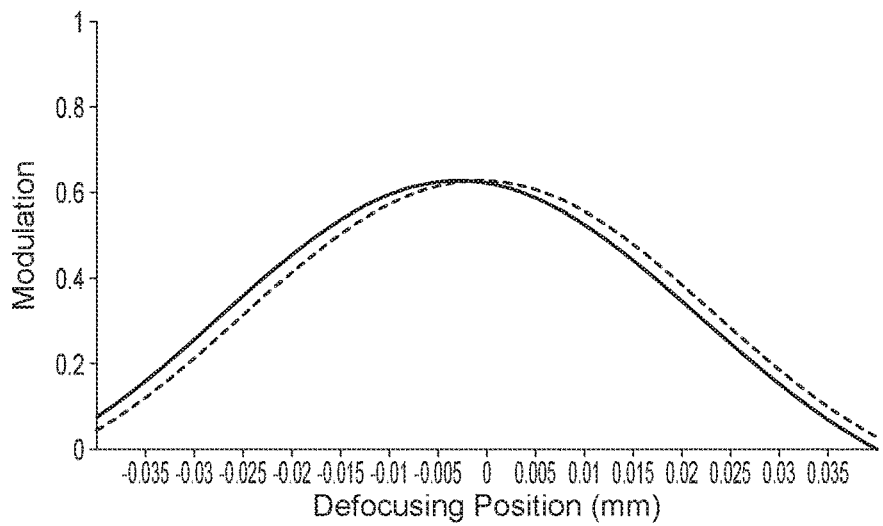
FIG. 17B is a diagram showing an astigmatism in an adhesive layer (wedge portion) of a polarizing beam splitter.
Figure 17C:
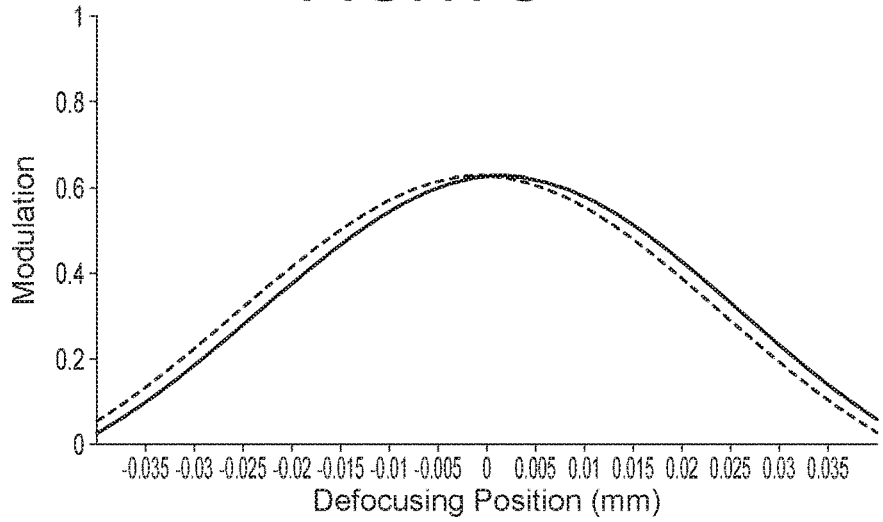
FIG. 17C is a diagram showing an astigmatism in a λ/4 wavelength plate of higher multi-order, in the example 5.

FIG. 17A shows an astigmatism at a final image plane. FIG. 17B shows an astigmatism in an adhesive layer 130 of polarizing beam splitters 121b and 121e. FIG. 17C shows an astigmatism after being transmitted through the λ/4 wavelength plate 121a of higher multi-order.

The astigmatism at the image plane shown in FIG. 17A is obtained by adding a characteristic curve shown in FIG. 17B and a characteristic curve shown in FIG. 17C. As it is evident from FIG. 17A, a difference between an astigmatism in a meridional direction and an astigmatism in a sagittal direction is reduced.

Accordingly, in the present example, it is possible to achieve an adequate depolarization and to reduce the astigmatism which occurs in the λ/4 wavelength plate of higher multi-order, thereby enabling to achieve a favorable image.

Example 6

Figure 18:
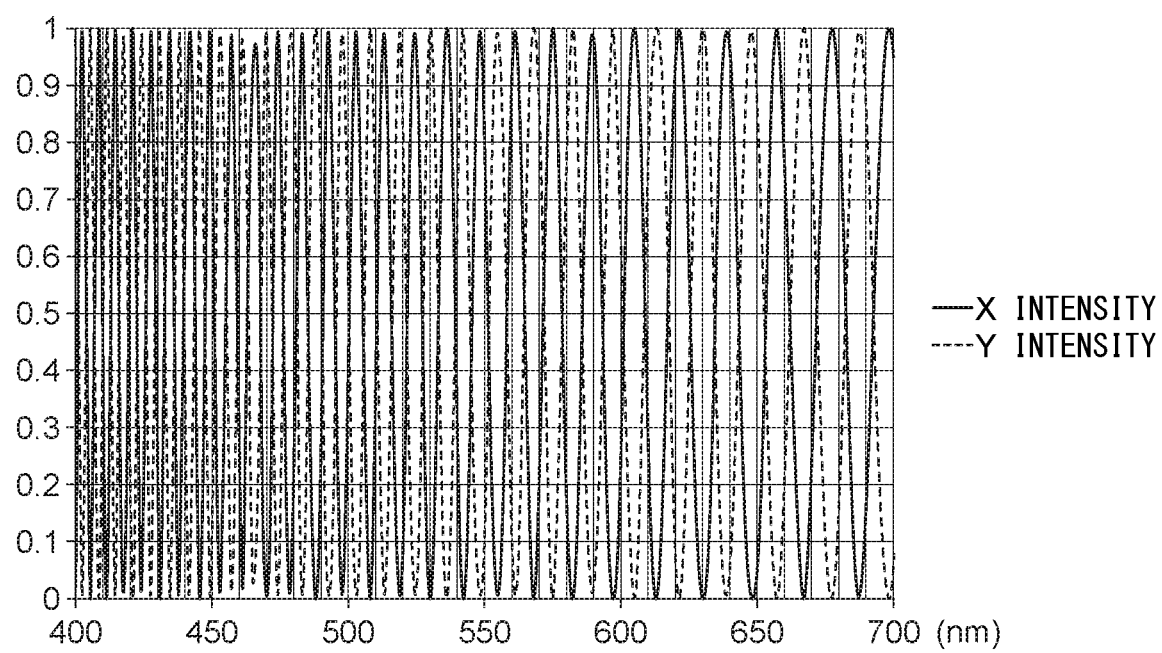
FIG. 18 is a diagram showing an optical characteristic of a λ/4 wavelength plate of higher multi-order of 38 wavelengths in an example 6.

An endoscope optical system according to an example 6 will be described below. FIG. 18 shows an optical characteristic of a λ/4 wavelength plate 121a of higher multi-order in an endoscope apparatus according to the example 6. It is an example of generating a phase difference of 38 wavelengths. The λ/4 wavelength plate 121a of higher multi-order having a large birefringence is disposed and used as a depolarization plate. For the λ/4 wavelength plate 121a, since a polarized wave varies at a high frequency in accordance with the wavelength, light passed through the λ/4 wavelength plate can be deemed as equivalent to unpolarized light in a visible range (400 nm 700 nm).

Figure 19A:
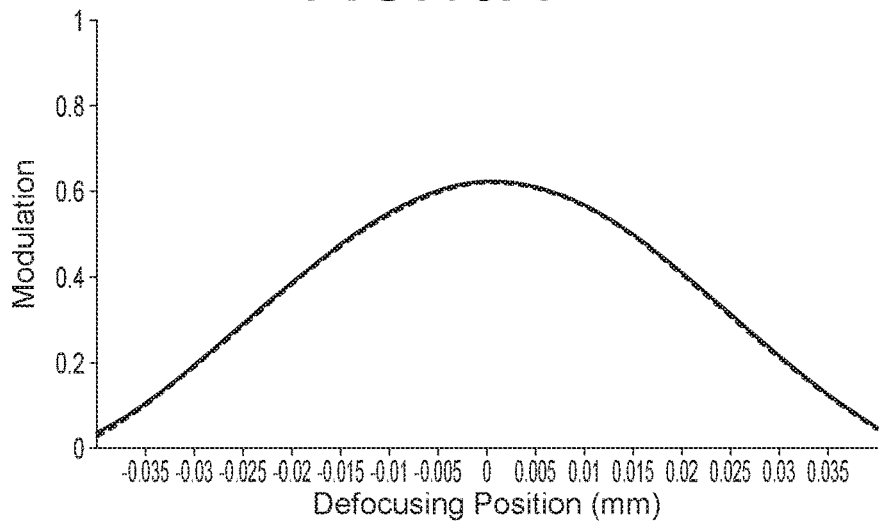
FIG. 19A is a diagram showing an astigmatism achieved finally.
Figure 19B:
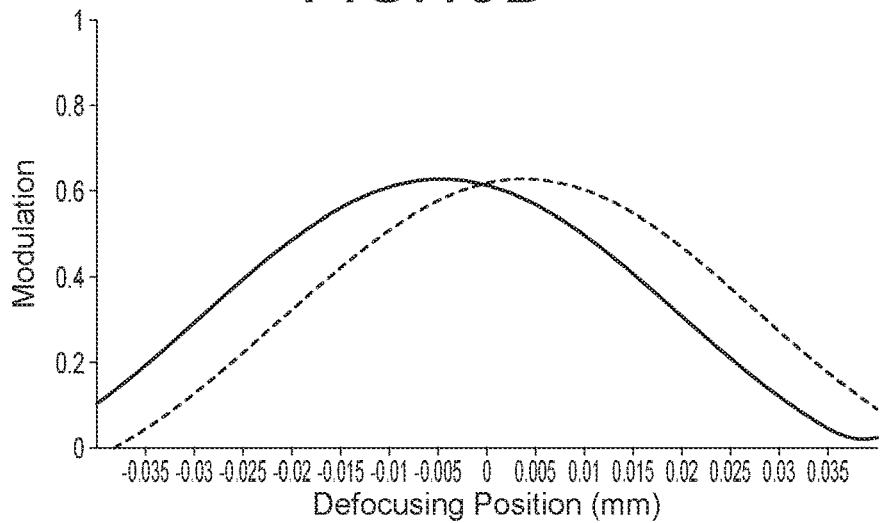
FIG. 19B is a diagram showing an astigmatism in an adhesive layer (wedge portion) of a polarizing beam splitter.
Figure 19C:
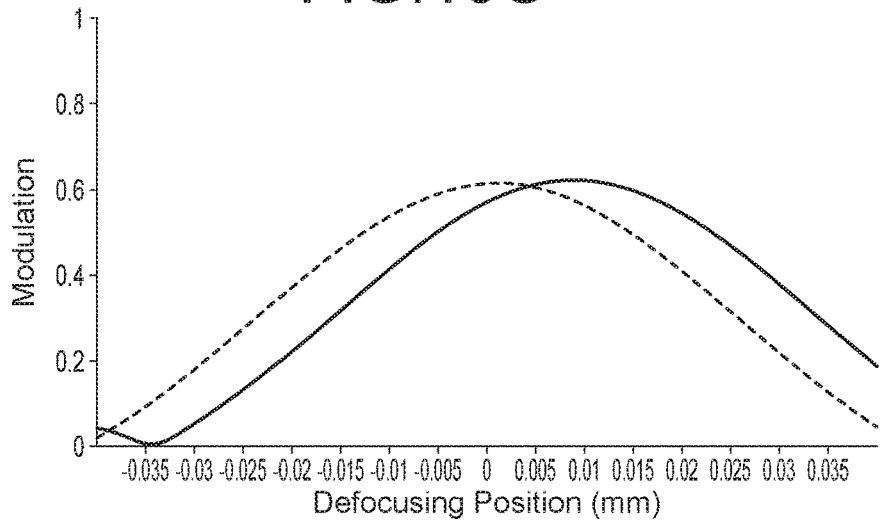
FIG. 19C is a diagram showing an astigmatism in a λ/4 wavelength plate of higher multi-order, in the example 6.

FIG. 19A shows an astigmatism at a final image plane. FIG. 19B shows an astigmatism in an adhesive layer 130 of polarizing beam splitters 121b and 121e. FIG. 19C shows an astigmatism after being transmitted through the λ/4 wavelength plate of higher multi-order.

The astigmatism at the image plane shown in FIG. 19A is obtained by adding a characteristic curve shown in FIG. 19B and a characteristic curve shown in FIG. 19C. As it is evident from FIG. 19A, a difference between an astigmatism in a meridional direction and an astigmatism in a sagittal direction is reduced.

Accordingly, in the present embodiment, it is possible to achieve an adequate depolarization and to reduce the astigmatism which occurs in the λ/4 wavelength plate of higher multi-order, thereby enabling to achieve a favorable image.

Example 7

An endoscope optical system according to an example 7 will be described below. An optical characteristic of a λ/4 wavelength plate 121a of higher multi-order in an endoscope apparatus according to the example 7 is same as that in the example 1 (refer to FIG. 7). Therefore, the description of optical characteristic is omitted.

Figure 20A:
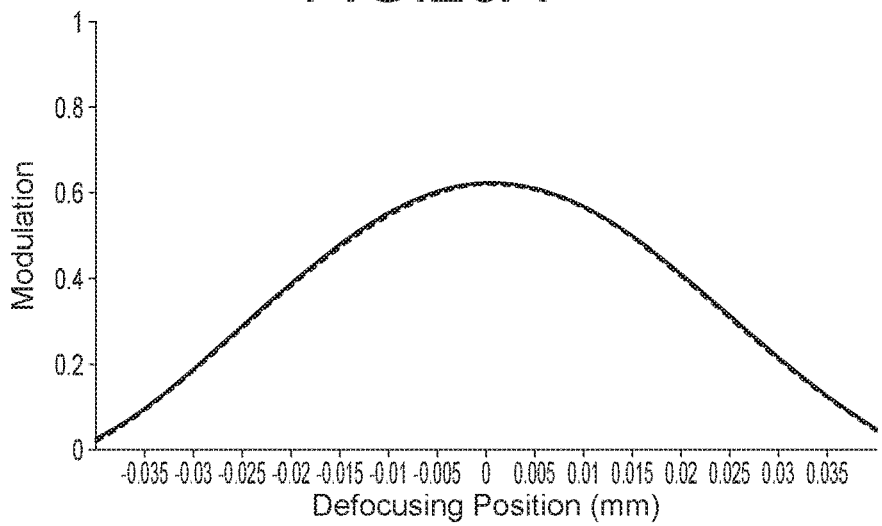
FIG. 20A is a diagram showing an astigmatism achieved finally.
Figure 20B:
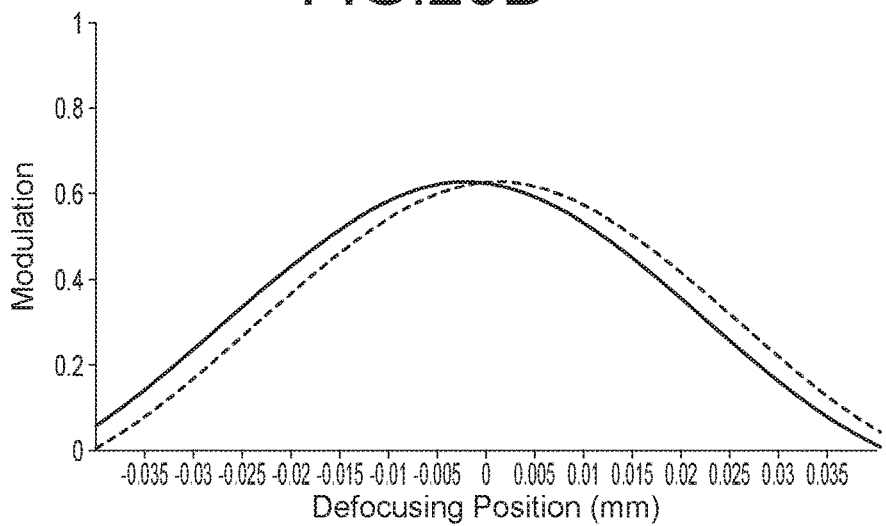
FIG. 20B is a diagram showing an astigmatism in an adhesive layer (wedge portion) of a polarizing beam splitter.
Figure 20C:
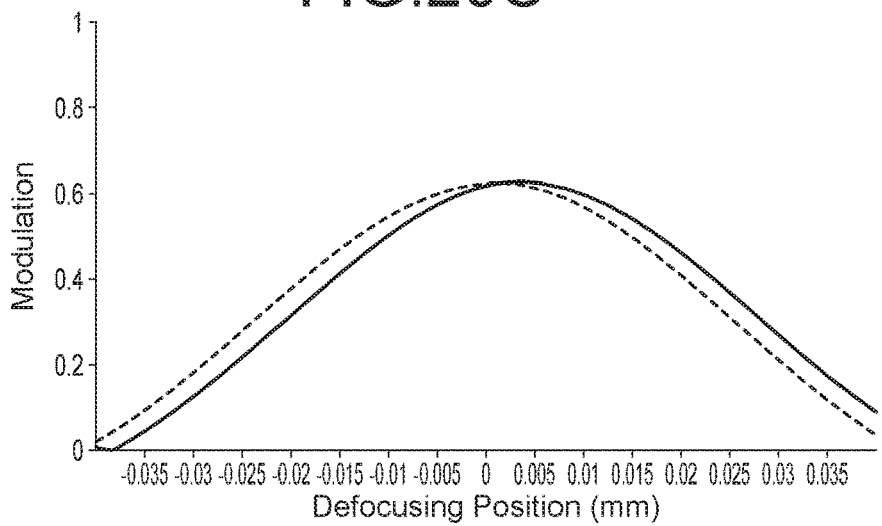
FIG. 20C is a diagram showing an astigmatism in a λ/4 wavelength plate of higher multi-order, in an example 7.

FIG. 20A shows an astigmatism at a final image plane. FIG. 20B shows an astigmatism in an adhesive layer 130 of polarizing beam splitters 121b and 121e. FIG. 20C shows an astigmatism after being transmitted through the λ/4 wavelength plate of higher multi-order.

The astigmatism at the image plane shown in FIG. 20A is obtained by adding a characteristic curve shown in FIG. 20B and a characteristic curve shown in FIG. 20C. As it is evident from FIG. 20A, a difference between an astigmatism in the meridional direction and an astigmatism in a sagittal direction is reduced.

Accordingly, in the present example, it is possible to achieve an adequate depolarization and to reduce the astigmatism which occurs in the λ/4 wavelength plate of higher multi-order, thereby enabling to achieve a favorable image.

Example 8

Figure 21:
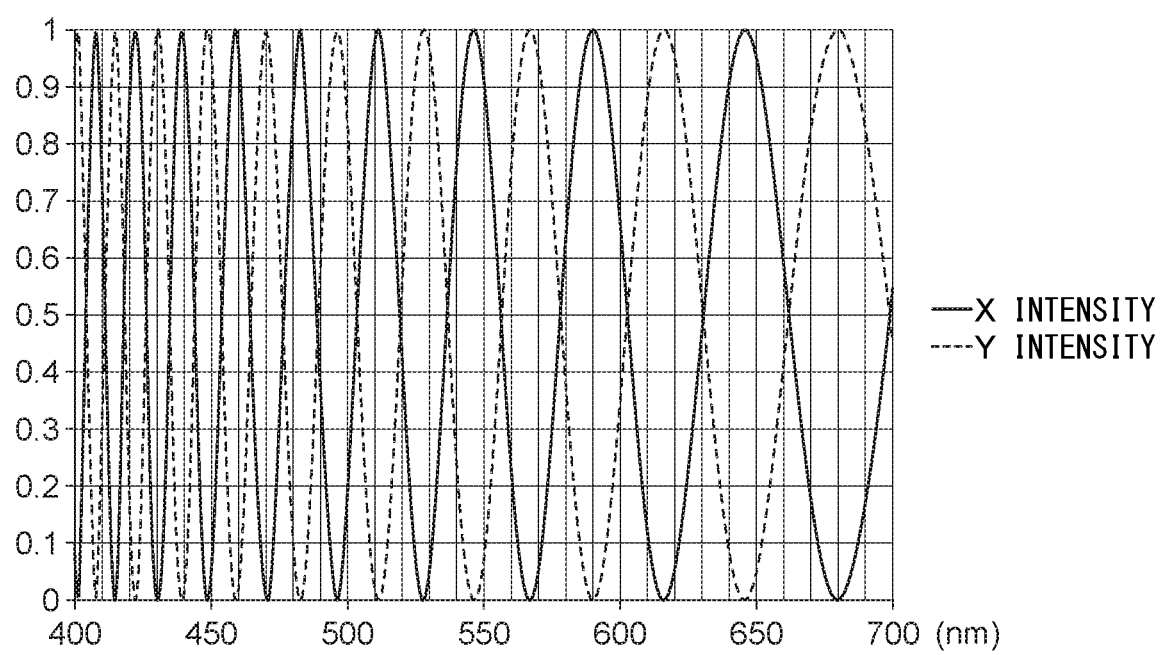
FIG. 21 is a diagram showing an optical characteristic of a λ/4 wavelength plate of higher multi-order of 10 wavelengths in an example 8.

An endoscope optical system according to an example 8 will be described below. FIG. 21 shows an optical characteristic of a λ/4 wavelength plate 121a of higher multi-order in an endoscope apparatus according to the example 8. It is an example of generating a phase difference of 10 wavelengths. The λ/4 wavelength plate 121a of higher multi-order having a large birefringence is disposed and used as a depolarization plate. For the λ/4 wavelength plate 121a of higher multi-order, since a polarized wave varies at a high frequency in accordance with the wavelength, light passed through the λ/4 wavelength plate can be deemed as equivalent to unpolarized light in a visible range (400 nm-700 nm).

Figure 22A:
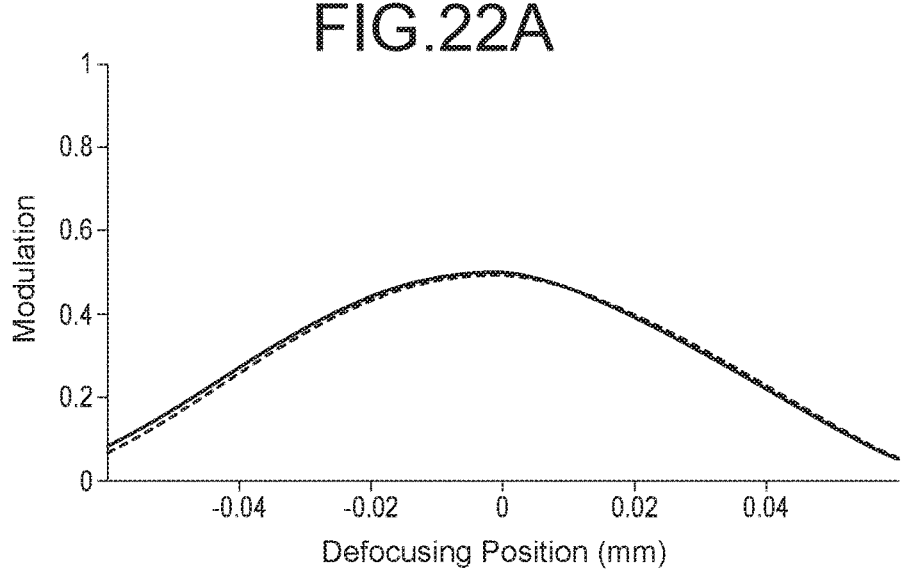
FIG. 22A is a diagram showing an astigmatism achieved finally.
Figure 22B:
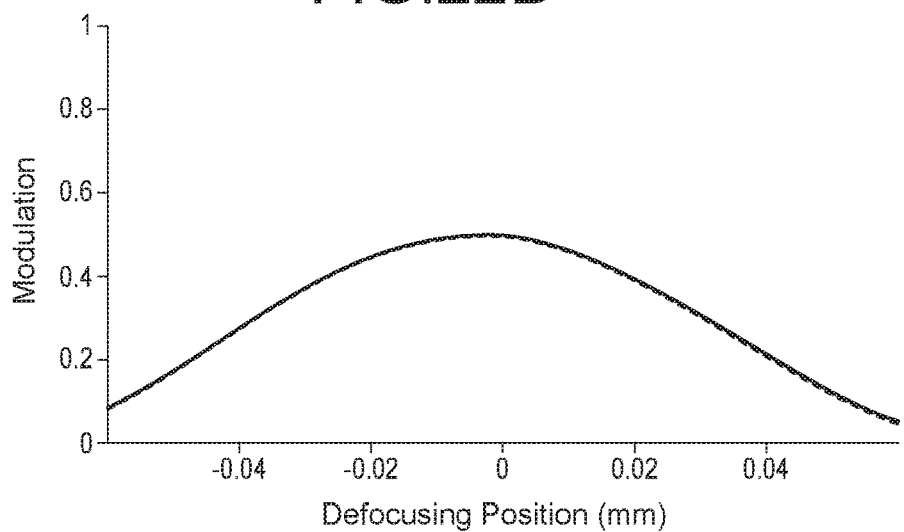
FIG. 22B is a diagram showing an astigmatism in an adhesive layer (wedge portion) of a polarizing beam splitter.
Figure 22C:
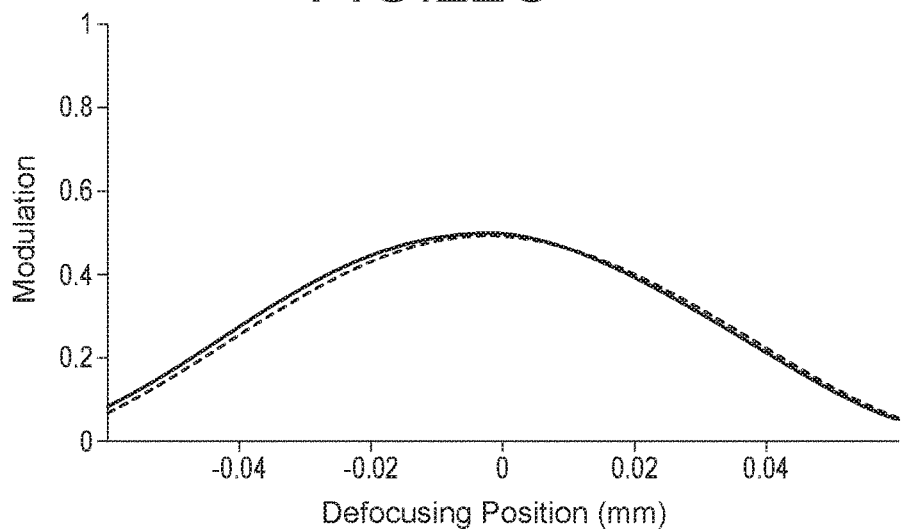
FIG. 22C is a diagram showing an astigmatism in a λ/4 wavelength plate of higher multi-order, in the example 8.

FIG. 22A shows an astigmatism at a final image plane. FIG. 22B shows an astigmatism in an adhesive layer 130 of polarizing beam splitters 121b and 121e. FIG. 22C shows an astigmatism after being transmitted through the λ/4 wavelength plate of higher multi-order.

The astigmatism at the image plane shown in FIG. 22A is obtained by adding a characteristic curve shown in FIG. 22B and a characteristic curve shown in FIG. 22C. As it is evident from FIG. 22A, a difference between an astigmatism in a meridional direction and an astigmatism in a sagittal direction is reduced.

Accordingly, in the present embodiment, it is possible to achieve an adequate depolarization and to reduce the astigmatism which occurs in the λ/4 wavelength plate of higher multi-order, thereby enabling to achieve a favorable image.

Note that, in the present example, the λ/4 wavelength plate (depolarization plate) of higher multi-order is not a material having a negative birefringence. Therefore, the astigmatism which occurs in the λ/4 wavelength plate of higher multi-order and the astigmatism which occurs in the polarizing beam splitter are not cancelled. However, the λ/4 wavelength plate of higher multi-order is made as thin as possible, and in addition, a refractive index of a glass material of the polarizing beam splitter is made small. Accordingly, in the present example, an absolute value of the astigmatism which occurs in the λ/4 wavelength plate of higher multi-order and an absolute value of the astigmatism which occurs in the polarizing beam splitter are made small.

(Various Data for Examples)

| Crystal material of λ/4 wavelength plate | Example1 minus LiNbO$_3$ | Example2 minus LiNbO$_3$ | Example3 minus LiNO$_3$ | Example4 minus LiNbO$_3$ |
|---|---|---|---|---|
| Fno | 3.75 | 3.6 | 3 | 4.5 |
| d | 0.1 | 0.15 | 0.1 | 0.35 |
| Δn | −0.08798 | −0.08798 | −0.08798 | 0.08798 |
| lpc | 0.01 | 0.02 | 0.005 | 0.015 |
| np | 1.64129 | 1.64129 | 1.75844 | 1.75844 |

| Crystal material of λ/4 wavelength plate | Example5 minus LiNbO$_3$ | Example6 minus calcite | Example7 minus α-BBO | Example8 plus YVO$_4$ |
|---|---|---|---|---|
| Fno | 3.6 | 3.75 | 4.7 | 5 |
| d | 0.12 | 0.12 | 0.07 | 0.0236 |
| Δn | −0.08798 | −0.17372 | −0.12377 | 0.23122 |
| lpc | 0.005 | 0.02 | 0.023 | 0.01 |
| np | 1.75844 | 1.75844 | 1.64129 | 1.51825 |

Characteristics of each example are shown below.

PBS denotes a polarizing beam splitter

EF denotes extremely favorable.

F denotes favorable.

SF denotes somewhat favorable.

|  | Depolarization effect | Adjustment of adhesive layer of PBS | Extinction ratio of PBS |
| --- | --- | --- | --- |
| Example 1 | F | F | F |
| Example 2 | F | EF | F |
| Example 3 | F | Not necessary | EF |
| Example 4 | EF | F | EF |
| Example 5 | F | Not necessary | EF |
| Example 6 | EF | EF | EF |
| Example 7 | F | EF | F |
| Example 8 | EF | F | F-SF |

An adjustment of an adhesive layer of a polarizing beam splitter will be described below.

Prisms 121b and 121e used in the polarizing beam splitter 121 generally have a manufacturing error of an angle. In a case in which the manufacturing error is relatively large, since there arises a difference between an imaging quality of an upper image and a lower image or a left-side image and a right-side image formed on the image forming surface I of the image sensor 122, it is not preferable. Therefore, it is desirable to tilt the prisms 121b and 121e relatively by using a spacing of the adhesive layer 130, and to carry out the adjustment to make uniform the imaging quality of an optical image at the image forming surface I. In examples 2, 6, and 7, by having the thickness of the adhesive layer 130 relatively large, a range in which the tilt adjustment can be made is widened, and an improvement in the imaging quality at the image forming surface I is facilitated. Whereas, the examples 3 and 5 are examples in which, the tilt adjustment is eliminated by carrying out precision processing of the prisms 121b and 121e. Any of the methods may be adopted upon taking into consideration a component cost and an adjustment cost.

An extinction ratio of the polarizing beam splitter will be described below by using FIG. 2.

It is desirable that intensity of light to be subjected to optical-path splitting in the polarizing beam splitter 121 is substantially same. In other words, a state in which, when the S-polarized light is incident on the polarization splitting film 121f, the S-polarized light is reflected with 100% intensity to the optical path A, and when the P-polarized light is incident on the polarization splitting element 121f, the P-polarized light is reflected with 100% intensity to the optical path B, is an ideal state. Generally, a ratio of such intensity split of the optical paths A and B is defined as the extinction ratio, and is used as an index of quality of PBS. The larger the difference between a refractive index of a material used for the polarizing beam splitter 121 (prism 121b) and a refractive index of a material used for the polarization splitting film, the favorable is the extinction ratio. However, in a case in which the difference between the refractive index of the polarizing beam splitter 121 (prism 121b) and the adhesive layer 130 is excessively large, the astigmatism which occurs is excessively large thereby causing degradation of image, and therefore it is desirable to contain the refractive index difference to be appropriate. In the examples 3, 4, 5, and 6, an improvement in the extinction ratio is facilitated by making a refractive index of a glass used for the prism 121b comparatively high. Whereas, in the example 8, by using a commonly-used glass material for the polarizing beam splitter 121 (prism 121b) instead of containing the extinction ratio within an acceptable quality, a polarizing beam splitter arrangement favorable from a cost point of view is provided.

Values of each of embodiments are shown below.
(1) $Fno/(d/|\Delta n|)$
(2) $(np/\Delta n)/(d/lpc)$
Conditional Expression

|  | Example1 | Example2 | Example3 | Example4 |
| --- | --- | --- | --- | --- |
| (1) | 3.30 | 2.11 | 2.64 | 1.13 |
| (2) | 1.87 | 2.49 | 1.00 | 0.86 |
|  | Example5 | Example6 | Example7 | Example8 |
| (1) | 2.64 | 5.43 | 8.31 | 48.99 |
| (2) | 0.83 | 1.69 | 4.36 | 2.78 |

An endoscope apparatus according to the embodiments includes an endoscope having the above-mentioned optical system and an image processor having an image combining processor which combines images picked by the image sensor into one image.

FIG. 23 illustrates a configuration of the endoscope apparatus. An endoscope system 1 according to the present embodiment includes an endoscope 2 inserted into a subject, a light source 3 configured to supply illumination light to the endoscope 2, a processor 4, and an image display device 5.

The processor 4 has a function of performing image processing, but also has other functions. The processor 4 includes an actuator controller 25, an image processor 30, and a controller 39. The image display device 5 displays an image signal generated with the processor 4 as an endoscope image.

The endoscope 2 includes an elongated insertion unit 6 to be inserted into the subject, and an operating unit 7 provided at the rear end of the insertion unit 6. A light guide cable 8 extends outward from the operating unit 7. One end of the light guide cable 8 is detachably connected with the light source 3 through a connection unit 8a. The light guide cable 8 includes a light guide 9 therein. Part of the light guide 9 is disposed inside the insertion unit 6.

The light source 3 includes therein a lamp 11, such as a xenon lamp, as the light source. The light source is not limited to the lamp 11, such as a xenon lamp, but a light emitting diode (abbreviated to "LED") may be used. The transmitted light quantity of the illumination light generated with the lamp 11, for example, white light, is regulated with a diaphragm 12. Thereafter, the illumination light is condensed with a condenser lens 13, and made incident on an incident end surface of the light guide 9. It is possible to change the aperture of the diaphragm 12 with a diaphragm driving unit 14.

The light guide 9 transmits the illumination light generated by the light source 3 to a distal end portion 6a of the insertion unit 6. The transmitted illumination light is emitted from the distal end surface of the light guide 9. An illumination lens 15 is disposed in the distal end portion 6a while facing the distal end surface. The illumination lens 15 emits the illumination light from an illumination window 15a. In this manner, the observation target region inside the subject is illuminated.

An observation window 20 is provided adjacent to the illumination window 15a in the distal end portion 6a. Light from the observation target region passes through the observation window 20, and is made incident on the inside of the distal end portion 6a. The objective optical system is disposed behind the observation window 20. The objective optical system is formed of a lens group 16 and an optical path splitter 120.

The lens group 16 includes a lens 16a and a lens 21. The lens 21 is movable along the optical axis. In this manner, focusing is performed. An actuator 22 is disposed to move the lens 21.

One image sensor 122 (not illustrated) is disposed on the optical path splitter 120. Two optical images are simultaneously formed on the light-receiving surface of the image sensor 122. The two optical images are imaged with the image sensor 122.

The operating unit 7 is connected with the processor 4 through a cable 24. A signal connector 24a is provided in a portion connected with the processor 4. Transmission of various types of information is performed between the endoscope 2 and the processor 4 through the cable 24. The signal connector 24a includes a correction parameter storage unit 37.

The correction parameter storage unit 37 stores therein correction parameters (or information of correction parameters) used for correction of the image. The correction parameters are different between individual endoscopes. It is assumed that an endoscope having unique endoscope identification information is connected with the processor 4. In this case, on the basis of the endoscope identification information, correction parameters peculiar to the connected endoscope are read from the correction parameter storage unit 37. Image correction is performed in an image correction processor 32 on the basis of the read correction parameters. Presence/absence of correction is determined by the controller 39.

Control of the actuator 22 is performed by the actuator controller 25. For this reason, the actuator 22 and the actuator controller 25 are connected through a signal line 23. Moreover, the image sensor is connected with the image processor 30 through a signal line 27a. The signal from the image sensor is input to the image processor 30. Information of a switch 26 provided in the operating unit 7 is also transmitted to the processor 4 through a signal line.

When the optical path length in the first optical path is slightly different from the optical path length in the second optical path, two optical images in focus are formed in front of and behind the image pickup surface. The shift quantities of the optical images from the image pickup surface are slight. For this reason, two optical images in focus only in a part of the region are formed on the image pickup surface.

The two optical images are imaged with the image sensor 122. An image signal acquired by imaging is input to the image processor 30 through the signal line 27a. The image processor 30 includes an image reader 31, the image correction processor 32, an image combining processor 33, a rear-stage image processor 34, an image output unit 35, and a light control unit 36.

In the image reader 31, image signals of a plurality of images are read from the input image signal. Herein, both the number of optical images and the number of images are two.

In the optical system forming two optical images, a geometrical difference may occur. Examples of the geometrical difference include a relative shift (difference) of the two optical images, such as a shift (difference) in magnification, a shift (difference) in position, and a shift (difference) in rotational direction. It is difficult to completely remove these differences in manufacturing of the objective optical system or the like. However, when the shift quantities of them increase, for example, a composite image looks double. For this reason, it is preferable to correct the geometrical difference described above in the image correction processor 32.

The image correction processor 32 performs image correction on the two read images. The image correction processor 32 performs, for example, processing to make at least one difference among a relative difference in magnification, a difference in position, and a difference in rotation agree between the two images.

In addition, the image correction processor 32 performs tone correction. For this reason, the image correction processor 32 includes a tone correction unit (not illustrated). In tone correction, the tone correction unit performs processing to make relative luminance and saturation of the two images substantially agree in at least one desired specific wavelength band. The tone correction may be performed by the image correction processor 32, without providing the tone correction unit.

The image correction processor 32 changes the luminance in one of the two images to substantially agree with the luminance in the other image. Moreover, the image correction processor 32 changes the saturation in one of the images to substantially agree with the saturation in the other image.

As described above, in a method of acquiring an image with a large depth of field, only in-focus regions are extracted from a plurality of images, and composition of the extracted regions is performed. In the endoscope according to the present embodiment, it is possible to reduce a difference in brightness and/or a difference in tone in a plurality of images. Accordingly, it is possible to reduce unevenness in brightness and/or a difference in tone in the composite image.

Moreover, in a method for improving the color reproducibility of the image, image composition using two images is performed. When a difference in brightness and a difference in tone occurs in two optical images, a difference in brightness and a difference in tone occurs also in two images acquired by imaging. In the endoscope according to the present embodiment, it is possible to reduce a difference in brightness and a difference in tone, even when a difference in brightness and a difference in tone occurs in a plurality of images. Accordingly, it is possible to further improve color reproducibility of the composite image.

In the image combining processor 33, first, contrast is compared using two images. This comparison is performed on each of the spatially equal pixel regions in the two images. Thereafter, the pixel region with the relatively high contrast is selected. Thereafter, one image is generated using the selected pixel region. As just described, one combine (composite) image is generated from two images. When a difference in contrast between two images is small, it suffices to generate a combine (composite) image after performing composite image processing to provide each of the images with a predetermined weight and add the weight to the images.

The rear-stage image processor 34 performs image processing, such as edge enhancement and gamma correction, on the composite image. The image output unit 35 outputs the image-processed image to the image display device 5.

In the light control unit 36, a light control signal to control brightness of light to the standard brightness is generated from the image read with the image reader 31. The light control signal is output to the diaphragm driving unit 14 of the light source 3. The diaphragm driving unit 14 regulates the opening quantity of the diaphragm (aperture stop) 12 so as to maintain the standard brightness in accordance with the light control signal.

Figure 24:
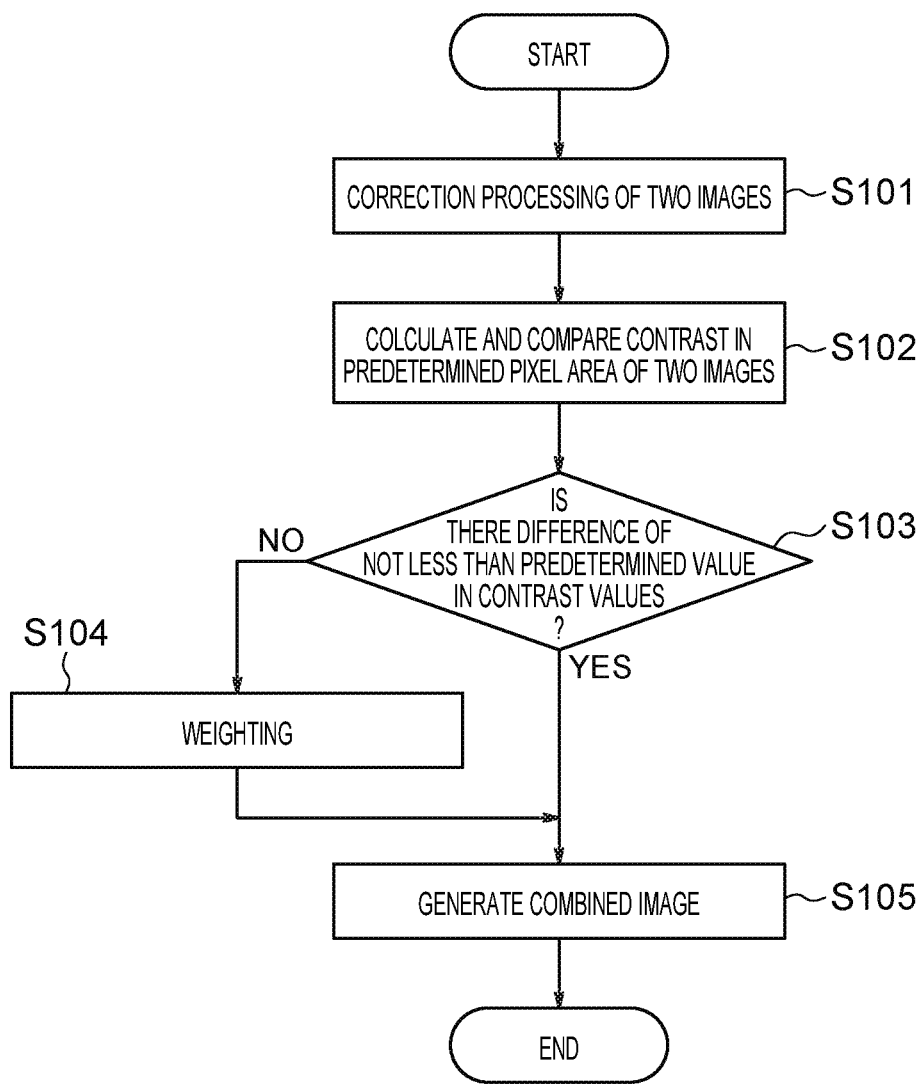
FIG. 24 is a flowchart showing a flow in a case of combining two optical images in the endoscope apparatus according to the embodiment.

Next, in the present embodiment, a flow in a case of combining two optical images will be described below according to a flowchart in FIG. 24.

An image related to the far-point image and an image related to the near-point image with a different focus are acquired in the image sensor 122. At step S101, the two images which are the near-point image and the far-point image, are subjected to correction processing. In other words, according to correction parameters that have been set in advance, correction of two images is carried out such that the relative position, the relative angle, and the relative magnification of each optical image of the two images becomes substantially same. This correction processing is carried out in the image correction processor 32. Images after correction are output to the image combining processor 33. The brightness and color of the two images may be corrected according to the requirement.

At step S102, the image combining processor 33 synthesizes the two images subjected to the correction processing. In other words, for the pixel area corresponding to each of the far-point image and the near-point image, a contrast value is calculated, and the contrast values are compared.

At step S103, a judgment of whether or not there is a difference in the contrast values that have been compared is made. In a case in which there is a difference in the contrast, the process advances to step S105. At step S105, the image combining is carried out. In a case in which there is a difference in the contrast, an area with a high contrast value is selected, and the images are combined.

In a case in which there is no difference in the contrast or in a case in which the difference in the contrast is small, the process advances to step S104.

In a case in which the difference in the contrast values is small or in a case in which the contrast values are almost same, it is necessary to make a judgment which to select between the two images which are the far-point image and the near-point image. Wrong choice of the selection becomes a cause of unstable processing. For instance, in a case in which a selected image includes a fluctuation in a signal such as noise, a discontinuous area occurs in the combined image or a problem such that an object image which is resolved originally becomes blurred occurs.

Therefore, the process advances to step S104 and the weighting is carried out. At step S104, in the pixel area in which the contrast is compared, in a case in which the contrast values for the two images which are the far-point image and the near-point image are almost same, the weighting is carried out. Moreover, the instability of the image selection is eliminated by carrying out an addition processing of images subjected to weighting at the subsequent step S105.

In such manner, according to the present embodiment, in both the close observation and the distant observation, it is possible to acquire an image in which the depth of field has been widened, while preventing the blurring of the optical image and the occurrence of the discontinuous area in the combined image due to noise.

FIG. 25 is a diagram showing an image-formation state in a case in which an image is formed on an image sensor after reflection for odd number of times by the polarization beam splitter 121. In a case of the abovementioned polarization beam splitter 121 in FIG. 25, an optical image is formed on the image sensor 122 after one reflection or in other words after reflection for the odd number of times. Consequently, one of the two images assume an image-formation state (mirror image) as shown in FIG. 8, and an image processing in which an image direction is made to coincide by inverting the mirror image in the image processor 30, is carried out.

Since correction of the mirror image by an optical reflection for the even number of times may lead to making the objective optical system large-size and the cost of the prism high, it is preferable to carry out the correction of the mirror image by reflection for the odd number of times by inverting the mirror image in the image correction processing section 32.

In a case in which the image sensor 122 has a shape which is long in a longitudinal direction of the endoscope, it is preferable to rotate the combined image appropriately up on taking into consideration an aspect ratio of the image display device 5.

Various embodiments of the present invention are described heretofore. However, the present invention is not restricted to these embodiments, and embodiments in which the arrangements of these embodiments are combined appropriately without departing from the scope of the invention also fall within the scope of the present invention.

As described heretofore, the present disclosure is useful for an endoscope optical system and an endoscope apparatus which enable to achieve a favorable image by reducing the astigmatism which occurs in a wavelength plate (depolarization plate) while achieving an adequate depolarization effect.

The present disclosure shows an effect that it is possible to provide an optical system, an endoscope apparatus and an whether endoscope which enable to achieve a favorable image by reducing the astigmatism which occurs in the λ/4 wavelength plate (depolarization plate) while achieving an adequate depolarization effect.

What is claimed is:

1. An optical system comprising in order from an object side:
    an objective optical system;
    a quarter-wave plate including one birefringent material, wherein a first axial astigmatism occurs in the quarter-wave plate;
    a polarizing beam splitter is configured to split light from the objective optical system into a transmitted light and a reflected light, wherein a second axial astigmatism occurs in the polarizing beam splitter; and
    an image sensor configured to pick up a first image of the transmitted light and a second image of the reflected light,
    wherein:
    the second axial astigmatism reduces the first axial astigmatism, and
    the following conditional expression (1) is satisfied:

$$1.1 \leq Fno/(d/|\Delta n|) \leq 49 \quad (1)$$

where:
Fno denotes an effective F-number of the objective optical system,
d denotes a thickness of the quarter-wave plate, and
$\Delta n$ denotes a birefringence of the quarter-wave plate for an e-line, provided that $|0.01| < \Delta n$.

2. The optical system according to claim 1, wherein the quarter-wave plate is disposed between an aperture stop of the objective optical system and an optical-path splitting surface of the polarizing beam splitter.

3. The optical system according to claim 2, wherein the quarter-wave plate is a uniaxial crystal material having a negative birefringence.

4. The optical system according to claim 3, wherein the following conditional expression (2) is satisfied:

$$0.8 \leq (np/\Delta n)/(d/lpc) \leq 4.4 \quad (2)$$

where:
np denotes a refractive index for an e-line of a glass material used for the polarizing beam splitter,
Δn denotes the birefringence of the quarter-wave plate for the e-line (546.1 nm), provided that |0.01|<Δn,
d denotes the thickness of the quarter-wave plate, and
lpc denotes a thickness of an adhesive layer of an adhesive used on a surface of the polarizing beam splitter.

5. An endoscope apparatus comprising:
an endoscope having the optical system according to claim 1; and
an image processor configured to combine the first image and the second image picked by the image sensor into one image.

6. An endoscope comprising:
the optical system according to claim 1.

7. The optical system according to claim 1, wherein the following conditional expression (1)' is satisfied, $$1.1 \leq Fno/(d/|\Delta n|) \leq 8.31 \quad (1)'$$

8. The optical system according to claim 1, wherein the following conditional expression (2)' is satisfied:

$$0.8 \leq (np/\Delta n)/(d/lpc) \leq 2.78 \quad (2)'$$

where:
np denotes a refractive index for an e-line of a glass material used for the polarizing beam splitter,
Δn denotes the birefringence of the quarter-wave plate for the e-line (546.1 nm), provided that |0.01|<Δn,
d denotes the thickness of the quarter-wave plate, and
lpc denotes a thickness of an adhesive layer of an adhesive used on a surface of the polarizing beam splitter.

9. The optical system according to claim 1, wherein the objective optical system comprises in order from the object side:
a first lens group having a negative refractive power;
a second lens group having a positive refractive power; and
a third lens group having a positive refractive power.

10. The optical system according to claim 9, wherein the first lens group comprises:
a planoconcave negative lens
a biconcave negative lens; and
a positive meniscus lens.

11. The optical system according to claim 9, wherein the second lens group comprises a positive meniscus lens.

12. The optical system according to claim 9, wherein the third lens group comprises:
a biconvex positive lens;
a negative meniscus lens;
a biconvex positive lens; and
a negative meniscus lens.

13. The optical system according to claim 5, wherein the image processor configured to:
acquire the first image and the second image; and
generate a combined image based on the first image and the second image.

14. The optical system according to claim 9, wherein the third lens group has an aperture stop.

15. The optical system according to claim 1, wherein the quarter-wave plate is a uniaxial crystal material having a negative birefringence.

16. The optical system according to claim 1, wherein the following conditional expression (2) is satisfied:

$$0.8 \leq (np/\Delta n)/(d/lpc) \leq 4.4 \quad (2)$$

where:
np denotes a refractive index for an e-line of a glass material used for the polarizing beam splitter,
Δn denotes the birefringence of the quarter-wave plate for the e-line (546.1 nm), provided that |0.01|<Δn,
d denotes the thickness of the quarter-wave plate, and
lpc denotes a thickness of an adhesive layer of an adhesive used on a surface of the polarizing beam splitter.

17. An endoscope comprising:
the optical system according to claim 2.

18. An endoscope comprising:
the optical system according to claim 4.

19. An endoscope comprising:
the optical system according to claim 15.

20. An endoscope comprising:
the optical system according to claim 16.

* * * * *